(12) United States Patent
Hu et al.

(10) Patent No.: US 6,229,012 B1
(45) Date of Patent: May 8, 2001

(54) TRIAZINE COMPOSITIONS

(75) Inventors: Nan-Xing Hu, Oakville; Zoran D. Popovic; Beng S. Ong, both of Mississauga; Hany Aziz, Burlington, all of (CA)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 09/489,527

(22) Filed: Jan. 21, 2000

Related U.S. Application Data

(63) Continuation-in-part of application No. 09/164,753, filed on Oct. 1, 1998, now Pat. No. 6,057,048.

(51) Int. Cl.⁷ .................................................. C07D 251/24
(52) U.S. Cl. ............................................ 544/180; 544/216
(58) Field of Search ...................................... 544/216, 180

(56) References Cited

U.S. PATENT DOCUMENTS

| | | | |
|---|---|---|---|
| 3,172,862 | 3/1965 | Gurnee et al. | 252/301.3 |
| 3,530,325 | 9/1970 | Mehl et al. | 313/108 |
| 4,356,429 | 10/1982 | Tang | 313/503 |
| 4,448,222 | 5/1984 | Arakawa | 139/435 |
| 4,539,507 | 9/1985 | VanSlyke et al. | 313/504 |
| 4,720,432 | 1/1988 | Vanslyke et al. | 428/457 |
| 4,769,292 | 9/1988 | Tang et al. | 428/690 |
| 4,885,211 | 12/1989 | Tang et al. | 428/457 |
| 5,150,006 | 9/1992 | Vanslyke | 313/504 |
| 5,151,629 | 9/1992 | VanSlyke | 313/504 |
| 5,429,884 | 7/1995 | Namiki et al. | 428/690 |
| 5,516,577 | 5/1996 | Matsuura et al. | 428/212 |
| 5,846,666 | 12/1998 | Hu et al. | 428/690 |
| 5,891,587 | 4/1999 | Hu et al. | 428/690 |
| 5,925,472 | 7/1999 | Hu et al. | 428/690 |
| 5,932,363 | 8/1999 | Hu et al. | 428/690 |
| 5,942,340 | 8/1999 | Hu et al. | 428/690 |
| 5,952,115 | 9/1999 | Hu et al. | 428/690 |
| 6,057,048 | * 5/2000 | Hu et al. | 428/690 |

OTHER PUBLICATIONS

"Influence of the emission Site on the Running Durability of Organic Electroluminescent Devices", Hamada et al., *Jpn. J. Appl. Phys.*, vol. 34, (1995), pp. L824–L826.

"Aromatic Polyethers With 1,3,5-Triazine Units as Hole Blocking/Electron Transport Materials in ELDs", Fink et al., *Macromol. Symp.* 125, 151 to 155 (1997).

* cited by examiner

*Primary Examiner*—Richard L. Raymond
*Assistant Examiner*—Venkataraman Balasubramanian
(74) *Attorney, Agent, or Firm*—E. O. Palazzo

(57) ABSTRACT

A triazine compound of the formula

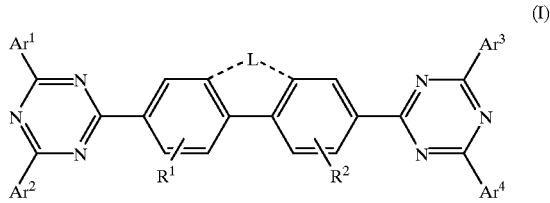

wherein $Ar^1$, $Ar^2$, $Ar^3$, and $Ar^4$ are each an aryl, aliphatic, or a mixture of aryl and aliphatic; $R^1$ and $R^2$ are selected from the group consisting of hydrogen, alkyl, aryl, alkoxy, halogen, and cyano; and L is L(n) wherein n is zero or 1, said L being a divalent group.

34 Claims, No Drawings

TRIAZINE COMPOSITIONS

This application is a continuation-in-part of U.S. Ser. No. 09/164,753, U.S. Pat. No. 6,057,048 the disclosure of which is totally incorporated herein by reference. The triazines of the present invention can be selected for the EL devices of copending application U.S. Ser. No. 09/164,753.

COPENDING APPLICATIONS

Illustrated in copending applications U.S. Ser. No. 09/489,144, and U.S. Ser. No. 09/489,754, disclosures of which are totally incorporated herein by reference, are triazines and electroluminescent devices containing triazines. The appropriate components and processes of the above copending applications may be selected for the present invention in embodiments thereof.

BACKGROUND OF THE INVENTION

The present invention is directed to organic electronic materials, and more specifically, to organic electron transport materials or luminescent materials comprised of novel triazine compounds, and which compounds can be selected for organic electroluminescent (EL) devices, and other optoelectronic devices including photoconductive devices and the like.

PRIOR ART

Organic electron transport materials or n-type organic semiconductors are useful for a number of device applications. For example, they can be selected for electron transport materials or luminescent materials in organic EL devices. An organic EL device with a multilayer structure can be formed as a dual layer structure comprising one organic layer adjacent to the anode supporting hole transport, and another organic layer adjacent to the cathode supporting electron transport and acting as the organic luminescent zone of the device. Another alternate device configuration for an EL device is comprised of three separate layers, a hole transport layer, a luminescent layer, and an electron transport layer, which layers are laminated in sequence and are sandwiched between an anode and a cathode. Optionally, a fluorescent dopant material can be added to the emission zone or layer whereby the recombination of charges results in the excitation of the fluorescent.

Typically, organic EL devices with multi-layered configurations comprise an anode, a hole transport layer, and an electron transport layer in contact with a cathode. This electron transport layer is intended to assist injection of electrons from the cathode. A known class of electron transport materials, which may also function as an luminescent layer, are the metal complexes of 8-hydroxyquinoline, as disclosed in U.S. Pat. Nos. 4,539,507, 4,720,432, and 5,151,629. A another known class of electron transport materials for EL devices are 1,3,5-oxidiazole compounds, such as those disclosed in *Japanese Journal of Applied Physics*, Part 2, vol. 34, L824 (1995), and 1,3,5-triazine a hole blocking layer in organic EL devices, reference Fink et al. in *Macromolecular Symposia*, vol. 125, 151 (1997).

While recent progress in organic EL research has elevated the potential of organic EL devices for widespread applications, the performance levels of current available devices may still be below certain expectations. Further, for visual display applications, organic luminescent materials should provide a satisfactory color in the visible spectrum, normally an emission maxima at about 460, 550 and 630 nanometers for blue, green and red. The metal complexes of 8-hydroxyquinoline, such as tris(8-hydroxyquinolinate) aluminum, generally fluoresce in green or a longer wavelength region, and which materials are suitable for use in EL devices with light emission in green or longer wavelength region. Although, a number of known electron transport materials may fluoresce in blue region, the performance characteristics of the EL devices may possess many disadvantages such as poor operation stability. Thus, there continues to be a need for electron transport materials for organic EL devices, which are suitable for the design of EL devices with satisfactory emission in the visible spectrum of, for example, from about 400 nanometers to about 700 nanometers. There is also a need for electron transport materials, which can enhance the EL charge transporting characteristics, thus desirably lowering device driving voltages; electron transport materials for EL devices comprised of a cathode comprised of a less active metal such as aluminum and which device can maintain desirable performance characteristics such as low driving voltage, and acceptable operation stability. Further, there is a need for electron transport materials, which are vacuum evaporable and can form thin films with excellent thermal stability. These and other needs and advantages can be achievable with the present invention in embodiments thereof.

SUMMARY OF THE INVENTION

It is an feature of the present invention to provide a class of triazine compounds, which can be selected for organic EL devices.

It is another feature of the present invention to provide a class of triazine compounds useful an optoelectronic materials that is for example, organic electron transport materials or fluorescent materials.

In an another feature of the present invention there is provided a class of triazine compounds with many advantageous properties, such as physical stability, for example a glass transition temperature exceeding about 100° C., photochemical stability, for example no detectable degradation under exposure to UV light, and electrochemical stability, for example reversible behavior in cyclic voltametry.

Further in another feature of the present invention there is provided triazine compounds with intense blue luminescence, including photoluminescence and electroluminescence.

Yet in another feature of the present invention there is provided triazine compounds comprised of two s-triazine rings covalently linked with a biphenyl unit.

Aspects of the present invention relate to triazine compounds illustrated by, or encompassed by the formula

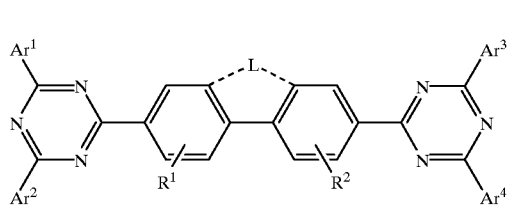

(I)

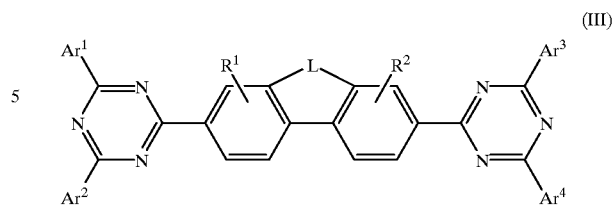

(III)

wherein $Ar^1$, $A^2$, $Ar^3$, and $Ar^4$ are each an aryl group, an aliphatic group, or a heteroaromatic group, wherein the aryl group contains for example, from about 6 to about 60 carbon atoms and preferably from about 6 to about 30 carbon atoms, which aryl group is more specifically independently selected for example, from the group consisting of a phenyl, a stilbenyl, a biphenylyl, a naphthyl, and the like; and wherein aliphatic refers primarily to alkyl; and heteroaromatic refers for example, to groups that may contain from about 2 to about 30 carbon atoms, and more specifically wherein the heteroaromatic is selected from the group consisting of a pyridyl, a quinolyl, a thienyl, a 1,3,5-oxadiazolyl and the like; and wherein the aryl group, aliphatic group or the heteroaromatic group may contain a suitable substituent selected for example, from the group consisting of hydrogen, an alkyl group with, for example, from 1 to about 6 carbon atoms, an aryl group with from 6 to about 30 carbon atoms, an alkoxy group with for example, from 1 to about 6 carbon atoms, a dialkylamino group with from about 1 to about 3 carbon atoms, a halogen, a cyano group and the like; $R^1$ and $R^2$ are each independently a substituent selected from the group consisting of hydrogen, an alkyl group with, for example, from 1 to about 6 carbon atoms, an alkoxy group with, for example, from 1 to about 6 carbon atoms, a halogen, a cyano group and the like; L which is optional, can be Ln wherein n is a number such as zero (no covalent bond) or 1, and which L when present is a suitable group, and preferably is a divalent group selected from the group consisting of an alkylene such as methylene or ethylene, a vinylene, an oxygen atom, a sulfur atom, —Si(R'R")—, wherein R' and R" are selected from the group consisting of hydrogen, alkyl, alkoxy, and aryl and the like; and preferably L is —C(R'R")—, wherein R' and R" is a hydrogen atom, an alkyl group containing from 1 to about 10 carbon atoms, or an alkoxyl group containing from 1 to about 10 carbon atoms, and the like.

Aspects of the present invention relate to; triazine compounds as represented by formula:

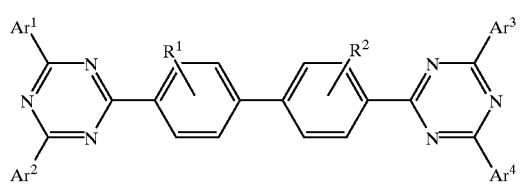

(II)

wherein the aryl groups of $Ar^1$, $Ar^2$, $Ar^3$, and $Ar^4$; and the substituents of $R^1$ and $R^2$ are as indicated herein; or by the formula wherein the substituents such as L, aryl groups of $Ar^1$, $Ar^2$, $Ar^3$, and $Ar^4$; and the substituents of $R^1$ and $R^2$ are as indicated herein.

The triazine compounds possess a number of advantageous properties, for example, these compounds possess electron transport properties, excellent physical stability, photochemical stability, and electrochemical stability; strong fluorescence in the blue region. The ability of forming films, with excellent thermal stability, by vacuum evaporation. Also, the triazine compounds can be selected as an electron transport component for organic electroluminescent devices such as those comprised of, for example, a supporting substrate of, for example, glass, an anode, an optional buffer layer, an organic hole transporting layer, an electron transport layer, and in contact therewith a low work function metal as a cathode, wherein the electron transport layer is comprised of the novel triazine compounds illustrated herein; an EL device comprised of in the following order, a supporting substrate of, for example, glass, an anode, an optional buffer layer, an organic hole transporting layer, a light emitting layer, an electron transport layer, and in contact therewith a low work function metal as a cathode, wherein the light emitting layer is comprised of the triazine compounds; or an EL device, wherein the electron transport layer is comprised of the triazine compounds. The use of the triazine compounds in EL devices can provide various improved performance characteristics, such as high luminance, low driving voltages, long device operation stability and durability, and enabling light emission from about 400 nanometers to about 700 nanometers. In addition, the EL devices containing the triazine compounds as an electron transport layer in contact with a cathode can permit use of a cathode comprised of an aluminum, and wherein the device can still maintains desirable performance characteristics such as low driving voltage, and acceptable operation stability.

DESCRIPTION OF EMBODIMENTS

The triazine compounds of the present invention can be illustrated by the formula

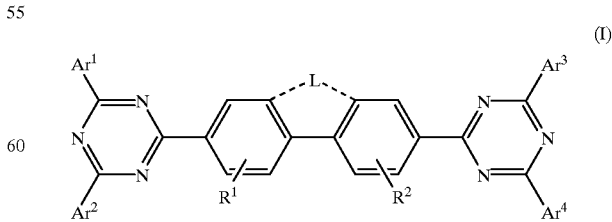

(I)

wherein each substituent is as illustrated herein, for example $Ar^1$, $A^2$, $Ar^3$, and $Ar^4$ are each an aryl group or a heteroaromatic group, wherein aryl contains, for example, from about 6 to about 60 carbon atoms and preferably from about 6 to about 30 carbon atoms, which may independently selected, for example, from the group consisting of a phenyl, a stilbenyl, a biphenylyl, a naphthyl, and the like; the heteroaromatic group may contain from about 2 to about 30 carbon atoms, and which group may independently be selected from the group consisting of a pyridyl, a quinolyl, a thienyl, a 1,3,5-oxadiazolyl and the like; and wherein the aryl group or the heteroaromatic group may further contain a substituent selected from the group consisting of hydrogen, an alkyl group with, for example, from 1 to about 12 carbon atoms, an aryl group with from about 6 to about 30 carbon atoms, an alkoxy group with, for example, from about 2 to about 20 carbon atoms, a dialkylamino group with from about 1 to about 3 carbon atoms, a halogen, a cyano group and the like; $R^1$ and $R^2$ are a substituent selected from the group consisting of hydrogen, an alkyl group having, for example, from 1 to about 6 carbon atoms, an alkoxy group having from 1 to about 6 carbon atoms, a halogen, a cyano group and the like; and L a divalent group, which may preferably be selected from the group consisting of an alkylene such as methylene or ethylene, a vinylene, —Si(R'R")—, an oxygen atom, a sulfur atom, and the like, and preferably L is a divalent group of —C(R'R")—, wherein R' and R" is a hydrogen atom, an alkyl group containing from 1 to about 10 carbon atoms, or an alkoxyl group containing from 1 to about 10 carbon atoms and wherein L is L(n) and wherein n is 10 zero, or 1.

In preferred embodiments, the triazine compounds of the present invention are encompassed by, or represented by the formula

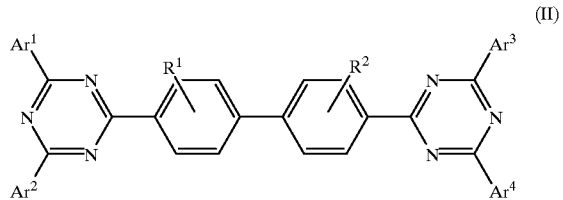

(II)

wherein the substituents are as illustrated herein, for example, the aryl groups of $Ar^1$, $Ar^2$, $Ar^3$, and $Ar^4$; are each independently aryl selected from the group consisting of a phenyl, a stilbenyl, a biphenylyl, a naphthyl, a pyridyl, and a quinolyl and the like, and preferably a phenyl or a naphthyl, and wherein the aryl group may further contain a substituent selected from the group consisting of hydrogen, an alkyl group with, for example, preferably from 1 to about 6 carbon atoms, an alkoxy group with, for example, preferably from 1 to about 6 carbon atoms, a dialkylamino group with preferably from about 1 to about 3 carbon atoms, a halogen, a cyano group and the like; $R^1$ and $R^2$ are substituents selected from the group consisting of hydrogen aliphatic such as an alkyl group, an alkoxy group, a halogen such as a chloride atom, and a cyano group.

In another preferred embodiment, the triazine compounds of the present invention are encompassed by or are represented by

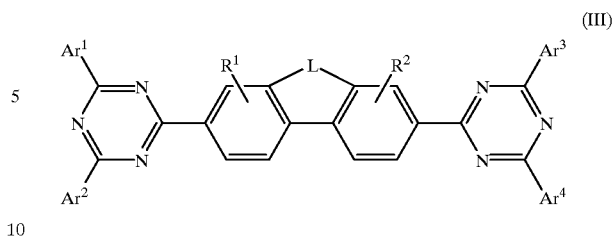

(III)

wherein the substituents are as illustrated herein, for example, aryl groups of $Ar^1$, $Ar^2$, $Ar^3$, and $Ar^4$; and L is a divalent group, such as those selected from the group consisting of alkylene such as methylene or ethylene, a vinylene, —Si(R'R")—, an oxygen atom, a sulfur atom, and the like, and preferably L is —C(R'R")—, wherein R' and R" is a hydrogen atom, an alkyl group containing from 1 to about 10 carbon atoms, a phenyl, an alkylphenyl, an alkoxyl group containing from 1 to about 10 carbon atoms, or an alkoxyphenyl, and the like.

Aryl of $Ar^1$ to $Ar^4$ is preferably selected from the group consisting of a phenyl, a tolyl, a butylphenyl, a methoxyphenyl, a naphthyl, and the like; the substituents $R^1$ and $R^2$ are preferably hydrogen, methyl, halogen atom such as a fluorine or chlorine, fluoride or chloride; L is a divalent group preferably selected from the group consisting of —C(R'R")—, an oxygen atom, a sulfur atom, and the like, and more preferably L is —C(R'R")—, wherein R' and R" is a hydrogen atom, an alkyl group containing from 1 to about 10 carbon atoms, a phenyl, an alkylphenyl, an alkoxyl group containing from 1 to about 10 carbon atoms, or an alkoxyphenyl, and the like.

The triazine compounds may be prepared by synthetic processes illustrated herein. In an illustrative example, the triazines such as those of Formula (III) can be synthesized as follows: a mixture of one equivalent of a suitable dicarbonyl halide, especially chloride compound such as 4,4'-biphenyidicarbonyl chloride or 4,4'-stilbene dicarbonyl chloride, from about 4 to about 6 equivalents of the corresponding aromatic nitrile compounds such as benzonitrile, m-tolunitrile, p-tolunitrile and the like, from about 2 to about 5 equivalents of aluminum chloride, and suitable amounts of an inert solvent, such as an organic solvent like o-dichlorobenzene, are first heated to from about 120 to about 200° C., and preferably from about 140 to about 160° C. for about a suitable period, for example from about 0.1 to about 1, and preferably about 0.5 hour; from about 2 to about 5 equivalents of ammonium chloride are then added, and the resulting reaction mixture is stirred for about 15 hours, or other suitable time. After cooling to room temperature of about 23° C., the reaction contents are added into an alcohol like methanol or water, and the resulting precipitate is collected by filtration. The product may further be purified by standard purification means including recrystallization and sublimation. The triazine compound products obtained may be confirmed by known elemental analysis, NMR or IR spectrometric identification techniques.

Specific examples of triazines compounds of the present invention include: 4,4'-bis-[2-(4,6-diphenyl-1,3,5-triazinyl)]-1,1'-biphenyl (II-1), 4,4'-bis-[2-(4,6-di-p-tolyl-1,3,5-triazinyl)]-1,1'-biphenyl (II-2), 4,4'-bis-[2-(4,6-di-m-tolyl-1,3,5-triazinyl)]-1,1'-biphenyl (II-3), 4,4'-bis-[2-(4,6-di-p-methoxyphenyl-1,3,5-triazinyl)]-1,1'-biphenyl (II-4), 4,4'-bis-[2-(4,6-di-m-methoxyphenyl-1,3,5-triazinyl)]-1,1'-biphenyl (II-5), 4,4'-bis-[2-(4-β-naphthyl-6-phenyl-1,3,5-triazinyl)]-1,1'-biphenyl (II-6), 4,4'-bis-[2-(4,6-di-biphenylyl-1,3,5-triazinyl)]-1,1'-biphenyl (II-7), 4-[2-(4,6-di-phenyl-1,3,5-triazinyl)]-4'-[(4,6-di-m-tolyl-1,3,5-triazinyl)]-1,1'-biphenyl (II-8), 2,7-bis-[2-(4,6-di-phenyl-1,3,5-triazinyl)]fluorene (III-1), 2,7-bis-[2-(4,6-di-phenyl-1,3,5-triazinyl)]-9,9-dimethylfluorene (III-2), 2,7-bis-[2-(4,6-di-phenyl-1,3,5-triazinyl)]-9,9-diethylfluorene (III-3), 2,7-bis-[2-(4,6-di-phenyl-1,3,5-triazinyl)]-9,9-diphenylfluorene (III-4), 2,7-bis-[2-(4,6-di-phenyl-1,3,5-triazinyl)]-9,10-dihydraphenanthrene (III-5), 4,9-bis-[2-(4,6-di-phenyl-1,3,5-triazinyl)]dibenzofuran(III-6), 4,9-bis-[2-(4,6-di-phenyl-1,3,5-triazinyl)]dibenzothiophene (III-7), 2,7-bis-[2-(4,6-di-phenyl-1,3,5-triazinyl)]-9,9-dimethyl-9-silafluorene (III-8), and the like.

II-1

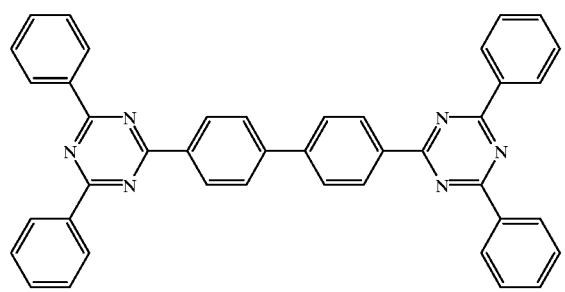

II-2

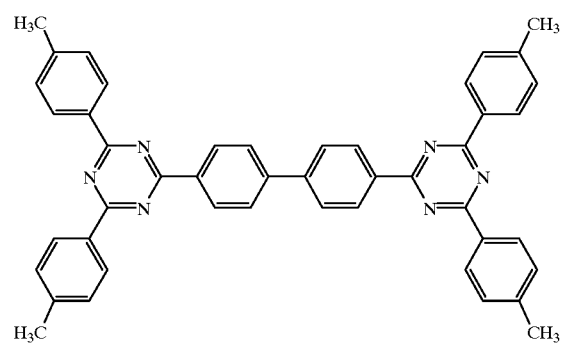

II-3

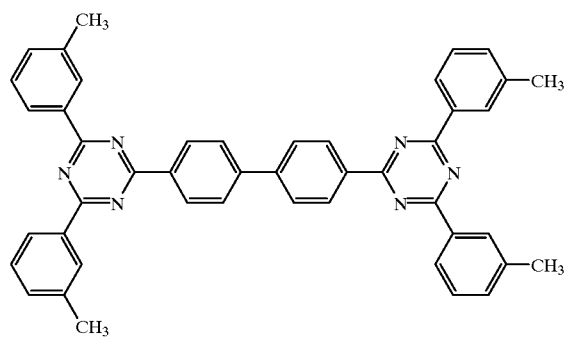

II-4

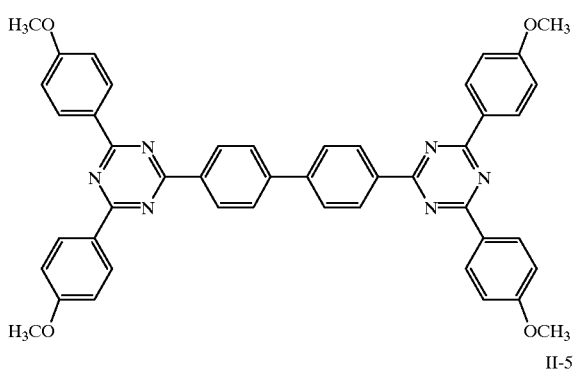

II-5

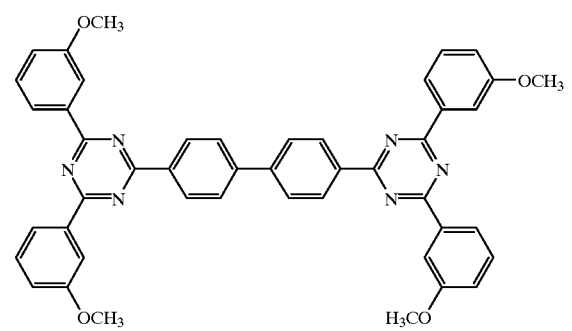

II-6

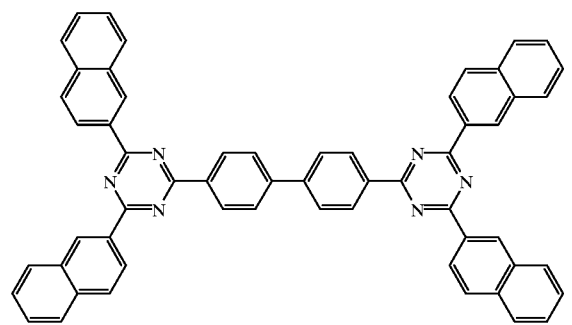

II-7

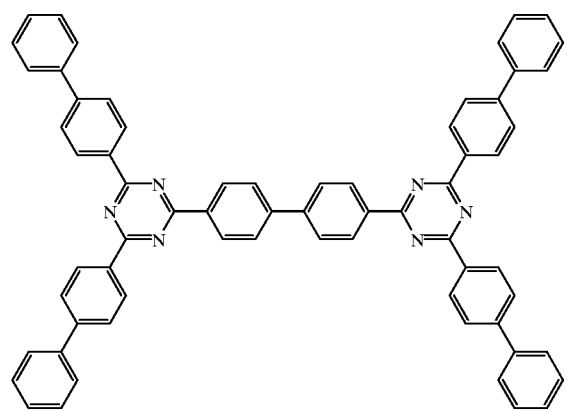

II-8

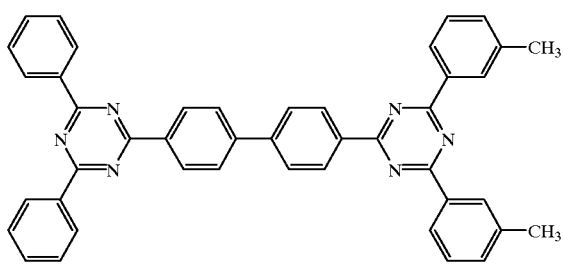

III-1

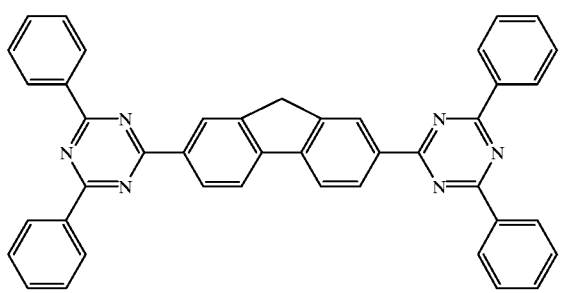

III-2

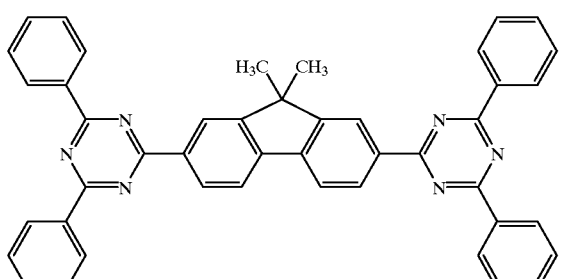

III-3

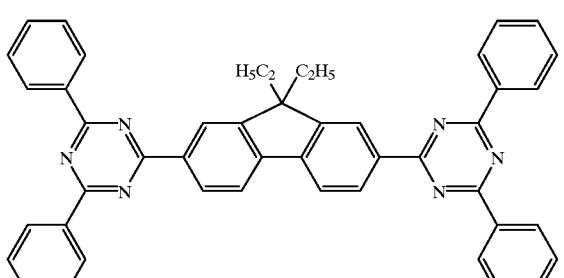

III-4

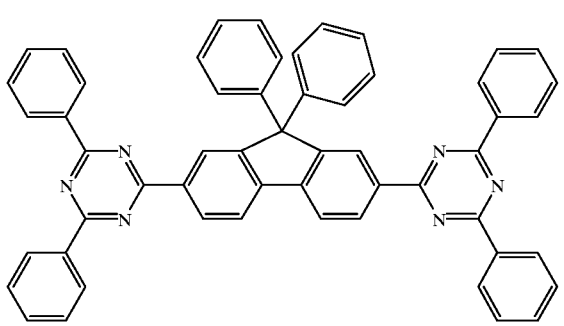

III-5

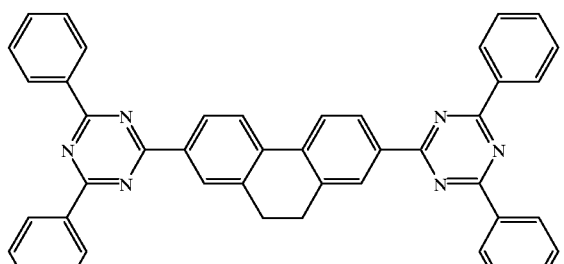

III-6

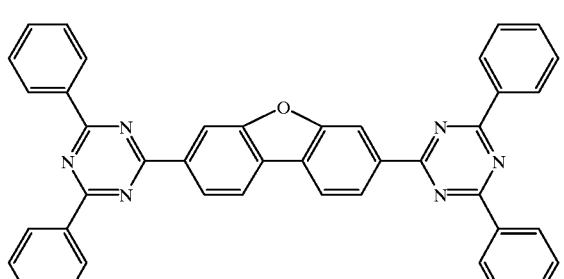

III-7

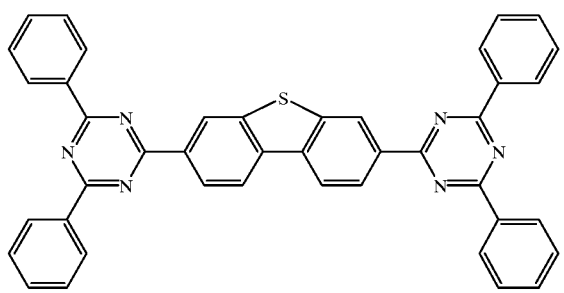

III-8

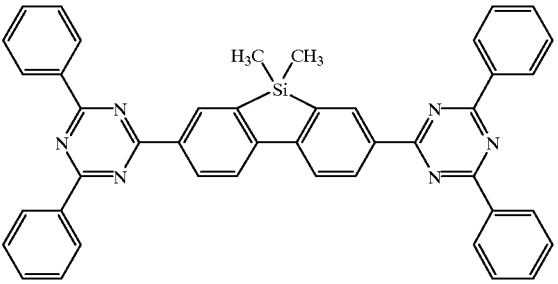

The triazines of the present invention can be selected for the EL devices of copending application U.S. Ser. No. 09/164,753, the disclosure of which is totally incorporated herein by reference, and more specifically, the triazines can be selected as a light emitting layer, an electron transporting layer and the like, wherein for example, the EL device is comprised of, for example, glass, an anode of, for example, indium tin oxide in a thickness of from about 1 to about 500 nanometers, preferably from about 30 to about 100 nanometers, a buffer layer of an aromatic amine compound in a thickness of from about 5 to about 300 nanometers, preferably from about 10 to about 100 nanometers, an organic hole transporting layer of, for example, 4,4'-bis-(9- carbazolyl)-1,1-biphenyl in a thickness of from about 1 to about 200 nanometers, preferably from about 5 to about 100 nanometers; an organic electron transport layer comprised of a triazine compound of the formulas illustrated herein in a thickness of from about 5 to about 300 nanometers, preferably from about 10 to about 100 nanometers, and in contact therewith a low work function metal as a cathode. In the EL device, either of the hole transport layer or the electron transport layer, can function as a light emitting layer. In embodiments, the EL device can be comprised of a supporting substrate of, for example, glass, an anode of, for example, indium tin oxide in a thickness of from about 1 to about 500 nanometers, preferably from about 30 to about 100 nanometers, a buffer layer thereover of an aromatic amine compound in a thickness from about 5 to about 300 nanometers, preferably from about 10 to about 100 nanometers, an organic hole transporting layer of, for example, N,N'-di-1-naphthyl-N,N'-diphenyl-1,1-biphenyl-4,4'-diamine in a thickness of from about 1 to about 200 nanometers, preferably from about 5 to about 100 nanometers, an organic light emitting layer thereover comprised of a triazine compound of the formulas illustrated herein in a thickness of from about 5 to about 300 nanometers, preferably from about 10 to about 100 nanometers, a conventional organic electron transporting layer of, for example, tris-(8-hydroxyquinolinato)aluminum in a thickness of from about 1 to about 300 nanometers, preferably from about 5 to about 100 nanometers, and in contact therewith a low work function metal as a cathode.

Illustrative examples of fluorescent materials are dyes selected for example, from the group consisting of coumarin, dicyanomethylene pyranes, polymethine, oxabenzanthrane, xanthene, pyrylium, carbostyl, perylene, and the like; a dye selected from the group consisting of quinacridone derivatives of, for example, the formula

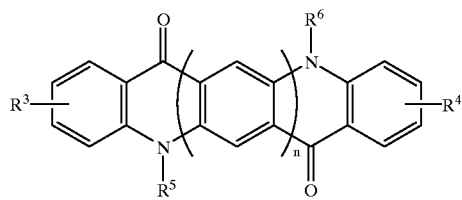

(IV)

wherein $R^3$ and $R^4$ are independently hydrogen, alkyl, alkoxyl, aryl, fused aryl, such as naphthyl, or halogen; $R^5$ and $R^6$ are independently hydrogen, alkyl or aryl; and n=0, 1, 2, or 3. Illustrative examples of quinacridone dyes include N,N'-dimethylquinacridone, N,N'-dimethyl-2-methyl quinacridone, N,N'-dimethyl-2,9-dimethylquinacridone, N,N'-dimethyl-2-chloroquinacridone, N,N'-dimethyl-2-fluoroquinacridone, and N,N'-dimethyl-1,2-benzoquinacridone. Another specially preferred class of fluorescent materials are quinacridone dyes. Illustrative examples of quinacridone dyes include quinacridone, 2-methylquinacridone, 2,9-dimethylquinacridone, 2-chloroquinacridone, 2-fluoroquinacridone, 1,2-benzoquinacridone, N,N'-dimethylquinacridone, N,N'-dimethyl-2-methylquinacridone, N,N'-dimethyl-2,9-dimethylquinacridone, N,N'-dimethyl-2-chloroquinacridone, N,N'-dimethyl-2-fluoroquinacridone, N,N'-dimethyl-1,2-benzoquinacridone, and the like. Also another preferred class of fluorescent materials are fused ring fluorescent dyes. Examples of the fused ring fluorescent dyes include perylene, rubrene, anthracene, coronene, phenanthrecene, pyrene and the like, as illustrated in U.S. Pat. No. 3,172,862, the disclosure of which is totally incorporated herein by reference. Also, fluorescent materials used as a dopant include butadienes, such as 1,4-diphenylbutadiene and tetraphenylbutadiene, and stilbenes, and the like as illustrated in U.S. Pat. Nos. 4,356,429 and 5,516,577, the disclosures of which are totally incorporated herein by reference.

The light emitting layer, which may be comprised of the triazine compounds illustrated herein of the present invention may be formed by any convenient manner. For example, this layer can be prepared by vacuum deposition from the simultaneous evaporation of the host layer material and the fluorescent dye. The thickness of the light emitting layer is not particularly limited, and can for example, be from about 5 nanometers to about 300 nanometers, and preferably from about 10 nanometers to about 100 nanometers.

Illustrative examples of the supporting substrate include polymeric components, glass and the like, and polyesters like MYLAR®, polycarbonates, polyacrylates, polymethacrylates, polysulfones, quartz, and the like. Other substrates can also be selected providing that the material can effectively support the other layers, and does not interfere with the device functional performance. The thickness of the substrate can be, for example, from about 25 to about 1,000 microns or more, and for example, from about 50 to about 500 depending, for example, on the structural demands of the device.

Examples of the anode which is contiguous to the substrate, include positive charge injecting electrodes such as indium tin oxide, tin oxide, gold, platinum, or other materials such as electrically conductive carbon, π-conjugated polymers such as polyaniline, polypyrrole, and the like, with a work function equal to, or greater than about 4 electron volts, and more specifically from about 4 to about 6 electron volts. The thickness of the anode can for example, be from about 1 to about 5,000 nanometers with a preferred range being dictated by the optical constants of the anode material. One preferred range of thickness is from about 30 to about 100 nanometers.

The buffer layer illustrated herein, which is optional, functions primarily to facilitate efficient injection of holes from the anode, and to improve the adhesion between the anode and the organic hole transporting layer, thus further improving the device operation stability. Useful examples of buffer layer materials include conductive materials such as polyaniline and its acid-doped forms, polypyrrole, poly (phenylene vinylene), and the semiconductive organic materials disclosed in U.S. Pat. No. 4,448,222, the disclosure of which is totally incorporated herein by reference; porphyrin derivatives disclosed in U.S. Pat. No. 4,356,429, the disclosure of which is totally incorporated herein by reference, such as 1,10,15,20-tetraphenyl-21H,23H-porphyrin copper (II); copper phthalocyanine, copper tetramethyl phthalocyanine; zinc phthalocyanine; titanium oxide phthalocyanine; magnesium phthalocyanine; and the like.

A preferred class of hole transporting materials employed and preferably coated on the buffer layer are aromatic tertiary amines such as those disclosed in U.S. Pat. No.

4,539,507, the disclosure of which is totally incorporated herein by reference. Representative examples of aromatic tertiary amines are bis(4-dimethylamino-2-methylphenyl) phenylmethane, N,N,N-tri(p-tolyl)amine, 1,1-bis(4-di-p-tolylaminophenyl)cyclohexane, 1,1-bis(4-di-p-tolylaminophenyl)-4-phenyl cyclohexane, N,N'-diphenyl-N, N'-bis(3-methylphenyl)-1,1'-biphenyl-4,4'-diamine, N,N'-diphenyl-N,N'-bis(3-methylphenyl)-1,1'-biphenyl-4,4'-diamine, N,N'-diphenyl-N,N'-bis( 4-methoxyphenyl)-1,1'-biphenyl-4,4'-diamine, N,N,N',N'-tetra-p-tolyl-1,1'-biphenyl-4,4'-diamine, N,N'-di-1-naphthyl-N,N'-diphenyl-1, 1'-biphenyl-4,4'-diamine, and the like. Another class of aromatic tertiary amines selected for the hole transporting layer is polynuclear aromatic amines, such as N,N-bis-[4'-(N-phenyl-N-m-tolylamino)-4-biphenylyl]aniline; N,N-bis-[4'-(N-phenyl-N-m-tolylamino)-4-biphenylyl]-m-toluidine; N,N-bis-[4'-(N-phenyl-N-m-tolylamino)-4-biphenylyl]-p-toluidine; N,N-bis-[4'-(N-phenyl-N-p-tolylamino)-4-biphenylyl]aniline; N,N-bis-[4'-(N-phenyl-N-p-tolylamino)-4-biphenylyl]-m-toluidine; N,N-bis-[4'-(N-phenyl-N-p-tolylamino)-4-biphenylyl]-p-toluidine; N,N-bis-[4'-(N-phenyl-N-p-chlorophenylamino)-4-biphenyly]-m-toluidine; N,N-bis-[4'-(N-phenyl-N-m-chlorophenylamino)-4-biphenyly]-m-toluidine; N,N-bis-[4'-(N-phenyl-N-m-chlorophenylamino)-4-biphenylyl]-p-toluidine; N,N-bis-[4'-(N-phenyl-N-m-tolylamino)-4-biphenylyl]-p-chloroaniline; N,N-bis-[4'-(N-phenyl-N-p-tolylamino)-4-biphenylyl]-m-chloroaniline; N,N-bis-[4'-(N-phenyl-N-m-tolylamino)-4-biphenylyl]-1-aminonaphthalene and the like.

The buffer layer comprised of aromatic tertiary amines described herein may further include, as disclosed in U.S. Pat. No. 5,846,666, the disclosure of which is totally incorporated herein by reference, a stabilizer comprised of certain hydrocarbon compounds. Useful examples of hydrocarbon stabilizers are rubrene, 4,8-diphenylanthracene, and the like.

The buffer layer can be prepared by forming one of the above compounds into thin film by known methods, such as vapor deposition or spin-coating. The thickness of buffer layer thus formed is not particularly limited, and can be in a range of from about 5 nanometers to about 300 nanometers, and preferably from about 10 nanometers to about 100 nanometers.

The hole transporting layer can be comprised of a hole transporting material with a thickness ranging for example, of from about 1 nanometer to about 200 nanometers, and preferably from about 5 nanometers to 100 nanometers. This layer can reduce the driving voltage of the device and improve the confinement of the injected charge recombination within the triazine light emitting layer. Any conventional suitable aromatic amine hole transporting materials described for the buffer layer may be selected for forming this layer.

A preferred class of hole transporting materials selected for forming the hole transporting layer is comprised of 4,4'-bis(9-carbazolyl)-1,1'-biphenyl compounds of the formula

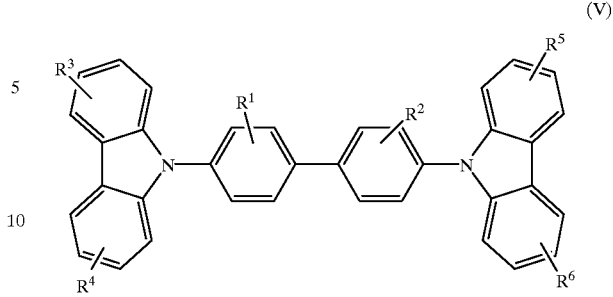

(V)

wherein $R^1$ and $R^2$ is hydrogen atom or an alkyl group of from 1 to about 3 carbon atoms; $R^3$ through $R^6$ are a substituent independently selected from the group consisting of hydrogen, alkyls having from about 1 to about 6 carbon atoms, alkoxyls having from about 1 to about 6 carbon atoms, halogen atom, dialkylamino groups, aryls, and the like. Illustrative examples of 4,4'-bis(9-carbazolyl)-1,1'-biphenyl compounds include 4,4'-bis(9-carbazolyl)-1,1'-biphenyl and 4,4'-bis(3-methyl-9-carbazolyl)-1,1'-biphenyl, or the like.

The EL device can be comprised of a light emitting layer comprised of the inventive triazine compounds and an electron transport layer comprised of a conventional electron transport materials for the purpose of improving the electron injection characteristics of the EL devices and the emission uniformity. The thickness of this layer can be from about 1 nanometers to about 300 nanometers, and preferably from about 5 nanometers to about 100 nanometers. Illustrative examples of electron transporting compounds, which can be utilized in this layer, include the metal chelates of 8-hydroxyquinoline as disclosed in U.S. Pat. Nos. 4,539, 507; 5,151,629 and 5,150,006 are totally incorporated herein by reference. Illustrative examples include tris(8-hydroxyquinolinate) aluminum, a preferred one, tris(8-hydroxyquinolinate) gallium, bis(8-hydroxyquinolinate) magnesium, bis(8-hydroxyquinolinate) zinc, tris(5-methyl-8-hydroxyquinolinate)aluminum, tris(7-propyl-8-quinolinolato) aluminum, bis[benzo{f}-8-quinolinate]zinc, bis(10-hydroxybenzo[h]quinolinate)beryllium, and the like. Another class of preferred electron injecting compounds are the metal thioxinoid compounds, illustrated in copending application U.S. Ser. No. 807,488, the disclosure of which is totally incorporated herein by reference. Illustrative examples of metal thioxinoid compounds include bis(8-quinolinethiolato)zinc, bis(8-quinolinethiolato)cadmium, tris(8-quinolinethiolato)gallium, tris(8-quinolinethiolato) indium, (preferred) bis(5-methylquinolinethiolato)zinc, tris (5-methylquinolinethiolato)gallium, tris(5-methylquinolinethiolato)indium, bis(5-methylquinolinethiolato)cadmium, bis(3-methylquinolinethiolato)cadmium, bis(5-methylquinolinethiolato)zinc, bis[benzo{f}-8-quinolinethiolato]zinc, bis[3-methylbenzo{f}-8-quinolinethiolato]zinc, bis[3,7-dimethylbenzo{f}-8-quinolinethiolato]zinc, and the like. Preferred are bis(8-quinolinethiolato)zinc, bis(8-quinolinethiolato)cadmium, tris(8-quinolinethiolato)gailium, tris(8-quinolinethiolato) indium and bis[benzo{f}-8-quinolinethiolato]zinc.

Yet another class of preferred electron transport materials are the oxadiazole metal chelates disclosed in copending application U.S. Ser. No. 829,398. Illustrative examples of the metal chelate compounds include bis[2-(2-hydroxyphenyl)-5-phenyl-1,3,4-oxadiazolato]zinc; bis[2-(2-hydroxyphenyl)-5-phenyl-1,3,4-oxadiazolato]beryllium; bis[2-(2-hydroxyphenyl)-5-(1-naphthyl)-1,3,4-oxadiazolato]zinc; bis[2-(2-hydroxyphenyl)-5-(1-naphthyl)-1,3,4-oxadiazolato]beryllium; bis[5-biphenyl-2-(2-hydroxyphenyl)-1,3,4-oxadiazolato]zinc; bis[5-biphenyl-2-(2-hydroxyphenyl)-1,3,4-oxadiazolato]beryllium; bis[2-hydroxyphenyl)-5-phenyl-1,3,4-oxadiazolato]lithium; bis[2-(2-hydroxyphenyl)-5-p-tolyl-1,3,4-oxadiazolato]zinc; bis[2-(2-hydroxyphenyl)-5-p-tolyl-1,3,4-oxadiazolato]beryllium; bis[5-(p-tert-butylphenyl)-2-(2-hydroxyphenyl)-1,3,4-oxadiazolato]zinc; bis[5-(p-tert-butylphenyl)-2-(2-hydroxyphenyl)-1,3,4-oxadiazolato]beryllium; bis[2-(2-hydroxyphenyl)-5-(3-fluorophenyl)-1,3,4-oxadiazolato]zinc; bis[2-(2-hydroxyphenyl)-5-(4-fluorophenyl)-1,3,4-oxadiazolato]zinc; bis[2-(2-hydroxyphenyl)-5-(4-fluorophenyl)-1,3,4-oxadiazolato]beryllium; bis[5-(4-chlorophenyl)-2-(2-hydroxyphenyl)-1,3,4-oxadiazolato]zinc; bis[2-(2-hydroxyphenyl)-5-(4-methoxyphenyl)-1,3,4-oxadiazolato]zinc; bis[2-(2-hydroxy-4-methylphenyl)-5-phenyl-1,3,4-oxadiazolato]zinc; bis[2-α-(2-hydroxynaphthyl)-5-phenyl-1,3,4-oxadiazolato]zinc; bis[2-(2-hydroxyphenyl)-5-p-pyridyl-1,3,4-oxadiazolato]zinc; bis[2-(2-hydroxyphenyl)-5-p-pyridyl-1,3,4-oxadiazolato]beryllium; bis[2-(2-hydroxyphenyl)-5-(2-thiophenyl)-1,3,4-oxadiazolato]zinc; bis[2-(2-hydroxyphenyl)-5-phenyl-1,3,4-thiadiazolato]zinc; bis[2-(2-hydroxyphenyl)-5-phenyl-1,3,4-thiadiazolato]beryllium; bis[2-(2-hydroxyphenyl)-5-(1-naphthyl)-1,3,4-thiadiazolato]zinc; and bis[2-(2-hydroxyphenyl)-5-(1-naphthyl)-1,3,4-thiadiazolato]beryllium, and the like.

Also, the EL device comprises an electron transport layer comprised of the inventive triazine compounds and a light emitting layer comprised of a conventional luminescent materials. Illustrative examples of luminescent materials, which can be utilized in this layer, include the metal chelates of 8-hydroxyquinoline as disclosed in U.S. Pat. Nos. 4,539,507, 5,151,629, and 5,150,006, the disclosures of which are totally incorporated herein by reference. Another class of luminescent materials comprised of fused ring aromatic hydrocarbons such as rubrene, perylene or 9,10-diphenylanthracene; butadiene derivatives, or stilbene derivatives, and the like. Illustrative examples of stilbene derivatives include those disclosed in U.S. Pat. No. 5,516,577, the disclosure of which is totally incorporated herein by reference, such as 4,4'-bis(2,2-diphenylvinyl)biphenyl and the like.

The cathode can be comprised of any metal, including high, for example a metal with a work function of from about 4.0 eV to about 6.0 eV, or low work function component, such as metals with, for example, an eV of from about 2.5 eV to about 4.0 eV (electron volts). The cathode can be derived from a combination of a low work function metal (less than about 4 eV) and at least one other metal. Effective proportions of the low work function metal to the second or other metal are from less than about 0.1 percent to about 99.9 percent by weight. Illustrative examples of low work function metals include alkaline metals such as lithium or sodium, Group 2A or alkaline earth metals such as beryllium, magnesium, calcium, or barium, and Group III metals including rare earth metals and the actinide group metals such as scandium, yettrium, lanthanum, cerium, europium, terbium, or actinium. Lithium, magnesium and calcium are the preferred low work function metals.

The thickness of cathode ranges from, for example, about 10 nanometers to about 500 nanometers. The Mg:Ag cathodes of Tang et al., reference U.S. Pat. No. 4,885,211, the disclosure of which is totally incorporated herein by reference, constitute one preferred cathode construction. Another preferred cathode construction is described in U.S. Pat. No. 5,429,884, wherein the cathodes are formed from lithium alloys with other high work function metals such as aluminum and indium.

Both the anode and the cathode of the EL devices of the present invention can be of any convenient forms. A thin conductive layer can be coated onto a light transmissive substrate, for example, a transparent or substantially transparent glass plate or plastic film. The EL device can include a light transmissive anode 3 formed from tin oxide or indium tin oxide coated on a glass plate. Also, very thin, for example less than 200 Å, light-transparent metallic anodes can be used, such as gold, palladium, and the like. In addition, transparent or semitransparent thin layer of conductive carbon or conjugated polymers such as polyaniline, polypyrrole, and the like can be used as anodes. Any light transmissive polymeric film can be employed as the substrate. Additional suitable forms of the anode and cathode are illustrated by Tang et al.

The following Examples are provided to further define various species of the present invention, it being noted that these Examples are intended to illustrate and not limit the scope of the present invention.

EXAMPLE I

Synthesis of 4,4'-Bis-[2-(4,6-diphenyl-1,3,5-triazinyl)]-1,1'-biphenyl:

In a 100 millimeters round bottom flask there was added 4,4'-biphenyldicarbonyl chloride (5.14 grams), 1,2-dichlorobenzene (15.0 millimeters), thionyl chloride (2.0 millimeters), and aluminum chloride (5.5 grams). With stirring, benzonitrile (7.6 grams) was added in about 15 minutes, and the resulting reaction mixture was heated under argon to about 150° C. for 0.5 hour. The temperature of the reaction mixture was reduced to 120° C., then ammonium chloride (3.5 grams) was added in one portion. The reaction mixture was stirred at this temperature of 120° C. for an additional 20 hours. The reaction flask was removed from the heater and cooled to room temperature, about 23° C. to about 25° C. throughout. The resulting mixture was poured into 600 millimeters of methanol and stirred for 20 minutes. The precipitates were collected by filtration and dried in a vacuum oven to afford 2.7 grams of crude product which was further purified by sublimation. The pure, about 99.5 percent purity, product of 4,4'-bis-[2-(4,6-diphenyl-1,3,5-triazinyl)]-1,1'-biphenyl had a melting point of 362° C. IR (KBr): 1588, 1564, 1525, 1445, 1368, 842, 827, 765, 690, 645 cm$^{-1}$.

H-NMR (CDCl$_3$-CF3COOD): δ 7.76 (t, J=7.8 Hz), 7.92 (t, J=7.8 Hz), 8.10 (d, J=8.6 Hz), 8.63 (d, J=8.4 Hz), 8.84 (d, J=8.6 Hz).

$^{13}$C-NMR(CDCl$_3$-CF3COOD): δ 129.1, 129.3, 130.3, 130.4, 130.9, 131.9, 137.8, 147.8, 169.1, 169.4.

EXAMPLE II

Synthesis of 4,4'-Bis-[2-(4,6-di-p-tolyl-1,3,5-triazinyl)]-1,1'-biphenyl:

In a 250 millimeters round bottom flask there was added 4,4'-biphenyldicarbonyl chloride (8.215 grams), 1,2-dichlorobenzene (65 millimeters), thionyl chloride (1.0 millimeters), and aluminum chloride (7.3 grams). With stirring, p-tolunitrile (13.5 grams) was added in about 15 minutes, and the resulting reaction mixture was heated under argon to about 150° C. for 0.5 hour. The temperature of the reaction mixture was reduced to 120° C., then ammonium chloride (7.13 grams) was added in one portion. The reaction mixture was stirred at this temperature for an additional 20 hours. The reaction flask was then removed from the heater and cooled to room temperature. The resulting mixture was poured into 600 millimeters of methanol and stirred for 20 minutes. The precipitates were collected by filtration and dried in a vacuum oven to afford 3.49 grams of crude product which was further purified by sublimation. The pure, 99.5 percent, product of 4,4'-bis-[2-(4,6-di-p-tolyl-1,3,5-triazinyl)]-1,1'-biphenyl had a melting point of 427° C. IR (KBr): 1609, 1585, 1526, 1406, 1369, 847, 800, 657, 582 cm$^{-1}$.

H-NMR (CDCl$_3$-CF3COOD): δ 2.53 (s), 7.55 (d, J=8.4 Hz), 8.06 (d, J=8.6 Hz), 8.52 (d, J=8.4 Hz), 8.79 (d, J=8.6 Hz).

$^{13}$C-NMR(CDCl$_3$-CF3COOD): δ 22.0, 126.5, 129.0, 130.6, 130.9, 131.1, 131.7, 147.5, 147.7, 150.6, 168.3, 169.2.

EXAMPLE III

Synthesis of 4,4'-Bis-[2-(4,6-di-m-tolyl-1,3,5-triazinyl)]-1,1'-biphenyl:

In a 200 millimeters round bottom flask there was added 4,4'-biphenyldicarbonyl chloride (8.0 grams), 1,2-dichlorobenzene (65.0 millimeters), thionyl chloride (1.6 millimeters), and aluminum chloride (7.6 grams). With stirring, m-tolunitrile (13.4 grams) was added in about 15 minutes, and the resulting reaction mixture was heated under argon to about 150° C. for 0.5 hour. The temperature of the reaction mixture was reduced to 120° C., then ammonium chloride (6.1 grams) was added in one portion. The reaction mixture was stirred at this temperature for additional 20 hours. The reaction flask was removed from the heater and cooled to room temperature. The mixture was poured into 100 millimeters of methanol and stirred for 20 minutes. The precipitates were collected by filtration and dried in a vacuum oven to afford 2.568 grams of crude product which was further purified by sublimation. The pure, 99.5 percent, product of 4,4'-bis-[2-(4,6-di-m-tolyl-1,3,5-triazinyl)]-1,1'-biphenyl had a melting point of 343° C. IR (KBr): 1608, 1566, 1527, 1486, 1353, 828, 780, 769, 697, 676, 647 cm$^{-1}$.

H-NMR (CDCl$_3$-CF3COOD): δ 2.57 (s), 7.60≦7.78 (m), 8.10 (d, J=8.6 Hz), 8.41 (s), 8.85 (d, J=8.6 Hz).

$^{13}$C-NMR(CDCl$_3$-CF3COOD): δ 21.0, 128.1, 129.0, 129.2, 130.2, 130.7, 131.0, 131.9, 138.8, 140.9, 147.7, 168.8, 169.8.

EXAMPLE IV

Synthesis of 4,4'-Bis-[2-(4,6-di-4-tert-butylphenyl-1,3,5-triazinyl)]-1,1'-biphenyl:

In a 250 millimeters round bottom flask there was added 4,4'-biphenyldicarbonyl chloride (8.6 grams), 1,2-dichlorobenzene (50 millimeters), thionyl chloride (1.0 millimeters), and aluminum chloride (8.7 grams). With stirring, 4-tert-butylbenzonitrile (20 grams) was added in about 15 minutes, and the resulting reaction mixture was heated under argon to about 150° C. for 0.5 hour. The temperature of the reaction mixture was reduced to 120° C., then ammonium chloride (6.7 grams) was added in one portion. The reaction mixture was stirred at 150° C. for an additional 20 hours. The reaction flask was then removed from the heater and cooled to room temperature. The resulting mixture was then poured into 600 millimeters of methanol and stirred for 20 minutes. The precipitates were collected by filtration and dried in a vacuum oven to afford 5.5 grams of crude product which was further purified by sublimation. The pure product, 99.8 percent, of 4,4'-bis-[2-(4,6-di-4-tert-butylphenyl-1,3,5-triazinyl)]-1,1'-biphenyl had a melting point of about 472° C.

H-NMR (CDCl$_3$-CF3COOD): δ 1.42 (s), 7.78 (d, J=8.7 Hz), 8.07 (d, J=8.7 Hz), 8.56 (d, J=8.7 Hz), 8.80 (d, J=8.7 Hz).

$^{13}$C-NMR(CDCl$_3$-CF3COOD): δ 30.70, 36.04, 126.48, 127.48, 128.99, 130.63, 130.81, 131.69, 147.50, 163.26, 168.41, 169.11.

EXAMPLE V

Synthesis of 4,4'-Bis-[2-(4,6-di-4-methoxyphenyl-1,3,5-triazinyl)]-1,1'-biphenyl:

In a 250 millimeter round bottom flask there was added 4,4'-biphenyldicarbonyl chloride (5.0 grams), 1,2-dichlorobenzene (30 millimeters), thionyl chloride (0.5 millimeter), and aluminum chloride (5.9 grams). With stirring, 4-methoxybenzonitrile (11.5 grams) was added in about 15 minutes, and the resulting reaction mixture was heated under argon to about 150° C. for 0.5 hour. The temperature of the reaction mixture was reduced to 120° C., then ammonium chloride (4.6 grams) was added in one portion. The reaction mixture was stirred at 150° C. for an additional 20 hours. The reaction flask was then removed from the heater and cooled to room temperature. The resulting mixture was then poured into 600 millimeters of methanol and stirred for 20 minutes. The precipitates were collected by filtration and dried in a vacuum oven to afford 4.5 grams of crude product which was further purified by sublimation. The pure product of 4,4'-bis-[2-(4,6-di-4-methoxyphenyl-1,3,5-triazinyl)]-1,1'-biphenyl showed H-NMR (CDCl$_3$-CF3COOD): δ 4.01 (s), 7.22 (d, J=8.4 Hz), 8.04 (d, J=8.5 Hz), 8.62 (d, J=8.5 Hz), 8.69 (d, J=8.5 Hz).

EXAMPLE VI

This Example illustrates that the triazine compounds can be used as electron transport or luminescent layer that is a light-emitting; and wherein electron transport refers the material's electrical nature; an electron transport materials is not necessary to provide light emitting. In the Example that follows, the triazine material serve both electron transport and light emitting functions) luminescent materials in organic EL devices. Organic EL devices were fabricated in the following manner:

1. A 500 Å indium tin oxide (ITO) anode coated glass substrate, the thickness of the glass substrate being about 1 millimeter, was cleaned with a commercial detergent, rinsed with deionized water and dried in a vacuum oven at 60° C. for 1 hour. Immediately before use, the glass was treated with UV ozone for 0.5 hour.

2. The ITO anode coated on the glass substrate was then placed in a vacuum deposition chamber. The deposition rate and layer thickness were controlled by an Inficon Model IC/5 controller. Under a pressure of about $5 \times 10^{-6}$ Torr, an 50 nanometers thick buffer was deposited on the ITO glass substrate through simultaneous evaporation of N,N'-1-naphthyl-N,N'-diphenyl-1,1'-biphenyl-4,4'-diamine at a rate of 0.6 nanometer/second and 5,10-diphenylanthracene at a rate of 0.03 nanometer/second from two independently controlled tantalum boats.

3. Onto the buffer layer was deposited a 30 nanometers hole transporting compound of 4,4'-bis(9-carbazolyl)-1,1'-biphenyl at a rate of 0.6 nanometer/second to form a 30 nanometers hole transporting layer.

4. A 50 nanometers thick electron transport layer, at a rate of 0.6 nanometer/second, and which transport functions as a light emitting layer, was then deposited by evaporation of the triazine, such as 4,4'-bis-[2-(4,6-diphenyl-1,3,5-triazinyl)]-1,1'-biphenyl generated by the processes of Examples I through IV.

5. A 100 nanometer cathode of a magnesium silver alloy was deposited at a total deposition rate of 0.5 nanometer/second onto the triazine layer above by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

The devices as prepared above were retained in a dry box which was continuously purged with nitrogen gas. Its performance was assessed by measuring its current-voltage characteristics and light output under a direct current measurement. The current-voltage characteristics were determined with a Keithley Model 238 High Current Source Measure Unit. The ITO electrode was always connected to the positive terminal of the current source. At the same time, the light output from the device was monitored by a silicon photodiode.

The light output from the above prepared organic EL device with the Example I triazine was 350 cd/m$^2$ when it was driven by a direct bias voltage of 8.5 volts. The EL color was very saturated blue with CIE color coordinates of X=0.147 and Y=0.099 measured by Minolta Chromameter CS-100. The device emitted blue light with a peak emission at 450 nanometers, indicating that the EL emission originates from the luminescent triazine layer.

EXAMPLE VII

An organic EL device was fabricated in accordance with Example V except that 4,4'-bis-[2-(4,6-di-p-tolyl-1,3,5-triazinyl)]-1,1'-biphenyl was utilized as the electron transport luminescent material in place of 4,4'-bis-[2-(4,6-diphenyl-1,3,5-triazinyl)]-1,1'-biphenyl. The light output from this organic EL device was 400 cd/m$^2$ when it was driven by a direct bias voltage of 8.0 volts. The EL color was blue with CIE color coordinates of X=0.145 and Y=0.087. The device emitted blue light with a peak emission at 448 nanometers, indicating that the EL emission originates from the luminescent triazine layer.

EXAMPLE VIII

An organic EL device was fabricated in accordance with Example V except that 4,4'-bis-[2-(4,6-di-m-tolyl-1,3,5-triazinyl)]-1,1'-biphenyl was utilized as the luminescent material in place of 4,4'-bis-[2-(4,6-diphenyl-1,3,5-triazinyl)]-1,1'-biphenyl. The light output from this organic EL device was 150 cd/m$^2$ when it was driven by a direct bias voltage of 9.5 volts. The device emitted blue light with a peak emission at 440 nanometers, indicating that the EL emission originates from the luminescent triazine layer.

EXAMPLE IX

An organic EL device was fabricated in accordance with Example V except that 4,4'-bis-[2-(4,6-diphenyl-1,3,5-triazinyl)]-stilbene was utilized as the luminescent material in place of 4,4'-bis-[2-(4,6-diphenyl-1,3,5-triazinyl)]-1,1'-biphenyl. The light output from this organic EL device was 250 cd/m$^2$ when it was driven by a direct bias voltage of 8.5 volts. The EL color was blue with CIE color coordinates of X=0.159 and Y=0,161. The device emitted blue light with a peak emission at 453 nanometers, indicating that the EL emission originates from the luminescent triazine layer.

COMPARATIVE EXAMPLE 1

A control organic EL device was fabricated in accordance with Example V except that is 4,4'-(hexafluoroisopropylidene)-bis-[4-phenoxyphenyl-4-(4,6-diphenyl-1,3,5-triazine)] was utilized as the luminescent material in place of 4,4'-bis-[2-(4,6-diphenyl-1,3,5-triazinyl)]-1,1'-biphenyl. Under UV light this compound displays very weak fluorescence in the visible spectrum region because the two triazine moieties are linked with a non-conjugated group,

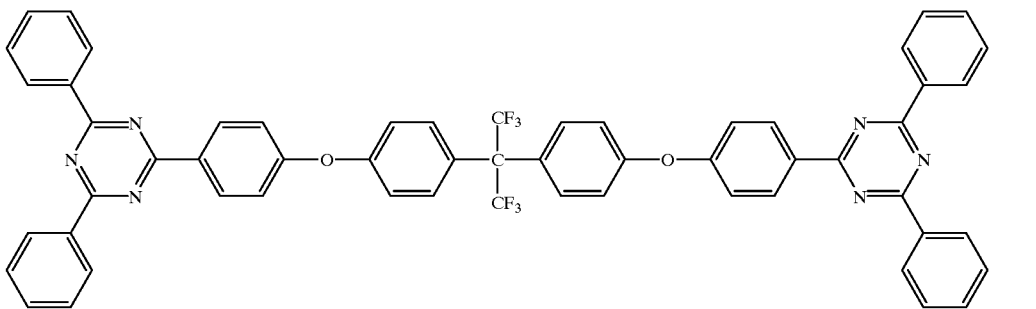

The light output from this organic EL device was not detectable when it was driven by a direct bias voltage. This Example indicates that a triazine compound linked by a non-conjugated bivalent group is apparently not as suitable as a light emitting component.

EXAMPLE X

This Example illustrates an organic EL device in which the inventive triazine compounds was selected as a light emitting layer.

1. A 500 Å indium tin oxide (ITO) anode coated glass substrate, the thickness of the glass substrate being about 1 millimeter, was cleaned with a commercial detergent, rinsed with deionized water and dried in a vacuum oven at 60° C. for 1 hour. Immediately before use, the glass was treated with UV ozone for 0.5 hour.

2. The ITO anode coated on the glass substrate was then placed in a vacuum deposition chamber. The deposition rate and layer thickness were controlled by an Inficon Model IC/5 controller. Under a pressure of about $5 \times 10^{-6}$ torr, a 50 nanometers thick buffer was deposited on the ITO glass substrate through simultaneous evaporation of N,N'-1-naphthyl-N,N'-diphenyl-1,1'-biphenyl-4,4'-diamine at a rate of 0.6 nanometer/second and 5,10-diphenylanthracene at a rate of 0.03 nanometer/second from two independently controlled tantalum boats.

3. Onto the buffer layer was deposited a 30 nanometer hole transporting compound of 4,4'-bis(9-carbazolyl)-1,1'-biphenyl at a rate of 0.6 nanometer/second to form a 30 nanometers hole transporting layer.

4. A 50 nanometers thick light emitting layer was then deposited by evaporation of 4,4'-bis-[2-(4,6-diphenyl-1,3,5-triazinyl)]-1,1'-biphenyl at a rate of 0.6 nanometer/second.

5. Onto the triazine light emitting layer was deposited a 30 nanometers thick electron transporting layer by evaporation of tris(8-hydroxyquinolinato)aluminum at a rate of 0.6 nanometer/second.

6. A 100 nanometer cathode of a magnesium silver alloy was deposited at a total deposition rate of 0.5 nanometer/second onto the tris(8-hydroxyquinolinato)aluminum layer above by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

The light output from this organic EL device was 350 cd/m$^2$ when it was driven by a direct bias voltage of 9.5 volts. The EL color was blue with CIE color coordinates of X=0.147 and Y=0.12. The device emitted blue light with a peak emission at 450 nanometers, indicating that the EL emission originates from the luminescent triazine layer.

EXAMPLE XI

This Example illustrated an organic EL device in which the inventive triazine compounds were selected as an electron transport layer. The device was fabricated in the following manner:

1. A 500 Å indium tin oxide (ITO) anode coated glass substrate, the thickness of the glass substrate being about 1 millimeter, was cleaned with a commercial detergent, rinsed with deionized water and dried in a vacuum oven at 60° C. for 1 hour. Immediately before use, the glass was treated with UV ozone for 0.5 hour.

2. The ITO anode coated on the glass substrate was then placed in a vacuum deposition chamber. The deposition rate and layer thickness were controlled by an Inficon Model IC/5 controller. Under a pressure of about $5 \times 10^{-6}$ Torr, a 60 nanometers thick hole transport layer was deposited on the ITO glass substrate through simultaneous evaporation of N,N'-1-naphthyl-N,N'-diphenyl-1,1'-biphenyl-4,4'-diamine at a rate of 0.5 nanometer/second and rubrene at a rate of 0.02 nanometer/second from two independently controlled tantalum boats.

3. Onto the hole transport layer was deposited a 75 nanometer light emitting layer through simultaneous evaporation of tris-(8-hydroxyquinolinato)aluminum at a rate of 0.5 nanometer/second and a fluorescent dye of rubrene at a rate of 0.02 nanometer/second from two independently controlled tantalum boats.

4. A 10 nanometer thick electron transport layer was then deposited on 3 above by evaporation of 4,4'-bis-[2-(4,6-diphenyl-1,3,5-triazinyl)]-1,1'-biphenyl at a rate of 0.6 nanometer/second.

5. A 100 nanometer cathode of a magnesium silver alloy was deposited at a total deposition rate of 0.5 nanometer/second onto the electron transport layer 4 by the simultaneous evaporation from two independently controlled tantalum boats containing Mg and Ag, respectively. A typical composition was 9:1 in atomic ratio of Mg to Ag. Finally, a 80 nanometer silver layer was overcoated on the Mg:Ag cathode for the primary purpose of protecting the reactive Mg from ambient moisture.

When driven by a direct bias voltage, the EL device emitted a yellow light with a peak emission at 560 nanometers, indicating that the EL emission originated from the rubrene dye. The device exhibited high luminance and satisfactory stability. Under a direct current density of 25 mA/cm$^2$, it provided a light intensity of about 1,480 cd/m$^2$, and maintained more than 75 percent of its initial luminance after continuous operation for 300 hours.

COMPARATIVE EXAMPLE 2

A control organic EL device was fabricated in accordance with Example X except that 2,4,6-triphenyl-1,3,5-triazine which was illustrated as Formula (V)

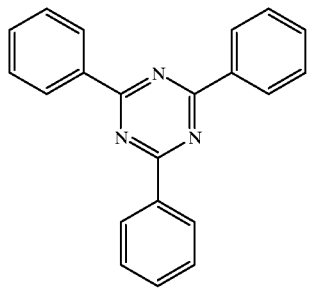

was utilized as the electron transport layer in place of layer 4, 4,4'-bis-[2-(4,6-diphenyl-1,3,5-triazinyl)]-1,1'-biphenyl. This compound does not contain an aromatic group comprised of at least two conjugate-linked or fused aromatic rings.

Under a direct current density of 25 mA/cm$^2$, it provided a light intensity of about 900 cd/m$^2$, and less than 20 percent of its initial luminance was detected after continuous operation for 10 hours. Thus, the device exhibited lower luminance and poorer stability compared to the devices of the present invention such as that of Example XI.

COMPARATIVE EXAMPLE 3

A control organic EL device was fabricated in accordance with Example XI except that 2,4,6-tri-2-pyridyl-1,3,5-triazine was utilized as the electron transport layer in place of layer 4,4,4'-bis-[2-(4,6-diphenyl-1,3,5-triazinyl)]-1,1'-biphenyl. This compound does not contain an aromatic group comprised of at least two conjugate-linked or fused aromatic rings.

Under a direct current density of 25 mA/cm$^2$, it provided a light intensity of about 1,350 cd/m$^2$, and less than 10 percent of its initial luminance was detected after continuous operation for 10 hours. Thus, the device exhibited poor stability.

COMPARATIVE EXAMPLE 4

A control organic EL device was fabricated in accordance with Example XI except that 2,4,6-triphenoxyl-1,3,5-triazine was utilized as the electron transport layer in place of layer 4,4,4'-bis-[2-(4,6-diphenyl-1,3,5-triazinyl)]-1,1'-biphenyl. This compound does not contain an aromatic group comprised of at least two conjugate-linked or fused aromatic rings.

The device exhibited low luminance and poor stability. Under a direct current density of 25 mA/cm$^2$, it provided a light intensity of about 300 cd/m$^2$, and less than 30 percent of its initial luminance was detected after continuous operation for 10 hours.

EXAMPLE XII

This Example illustrated an organic EL device which utilizes aluminum as the cathode in contact with a triazine electron transport layer. The device was fabricated in the following manner:

1. A 500 Å indium tin oxide (ITO) anode coated glass substrate, the thickness of the glass substrate being about 1 millimeter, was cleaned with a commercial detergent, rinsed with deionized water and dried in a vacuum oven at 60° C. for 1 hour. Immediately before use, the glass was treated with UV ozone for 0.5 hour.

2. The ITO anode coated on the glass substrate was then placed in a vacuum deposition chamber. The deposition rate and layer thickness were controlled by an Inficon Model IC/5 controller. Under a pressure of about 5×10$^{-6}$ Torr, a 60 nanometers thick hole transport layer was deposited on the ITO glass substrate through simultaneous evaporation of N,N'-1-naphthyl-N,N'-diphenyl-1,1'-biphenyl-4,4'-diamine at a rate of 0.5 nanometer/second and rubrene at a rate of 0.02 nanometer/second from two independently controlled tantalum boats.

3. Onto the hole transport layer was deposited a 75 nanometer light emitting layer through simultaneous evaporation of tris-(8-hydroxyquinolinato)aluminum at a rate of 0.5 nanometer/second and a fluorescent dye of rubrene at a rate of 0.02 nanometer/second from two independently controlled tantalum boats.

4. A 10 nanometer thick electron transport layer was then deposited on 3 by evaporation of 4,4'-bis-[2-(4,6-diphenyl-1,3,5-triazinyl)]-1,1'-biphenyl at a rate of 0.6 nanometer/second.

5. A 100 nanometer cathode of aluminum was deposited at a total deposition rate of 0.5 nanometer/second onto the electron transport layer by evaporation from a aluminum tantalum boat.

When driven by a direct bias voltage, the EL device emitted a yellow light with a peak emission at 560 nanometers, indicating that the EL emission originated from the rubrene dye. The device exhibited high luminance and satisfactory stability. Under a direct current density of 25 mA/cm$^2$, it provided a light intensity of about 1020 cd/m$^2$ with an initial voltage at 9.7 volts and maintained more than 75 percent of its initial luminance after continuous operation for 500 hours.

COMPARATIVE EXAMPLE 5

A control organic EL device was fabricated in accordance with Example XII except that tris-(8-hydroxyquinolinato) aluminum was utilized as the electron transport layer in place of layer 4, 4,4'-bis-[2-(4,6-diphenyl-1,3,5-triazinyl)]-1,1'-biphenyl in step 4.

Under a direct current density of 25 mA/cm$^2$ it provided a light intensity of about 800 cd/m$^2$ with an initial voltage at 10.5 volts, and about 25 percent of its initial luminance remained after continuous operation for 10 hours. Therefore, the device exhibited lower luminance and poorer stability compared to the device of Example XII.

Other modifications of the present invention will occur to those of ordinary skill in the art subsequent to a review of the present application. These modifications and equivalents thereof are intended to be included within the scope of the present invention.

What is claimed is:

1. A triazine compound of the formula

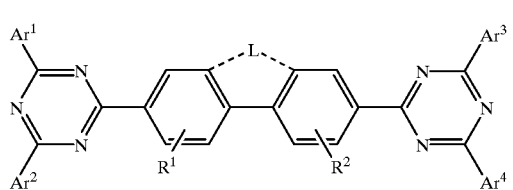

(I)

wherein $Ar^1$, $Ar^2$, $Ar^3$, and $Ar^4$ are each an aryl, aliphatic, or mixtures thereof; $R^1$ and $R^2$ are selected from the group consisting of hydrogen, alkyl, aryl, alkoxy, halogen, and cyano; and L is L(n) wherein n is zero or 1, said L being a divalent group.

2. A triazine compound in accordance with claim 1 wherein $Ar^1$, $Ar^2$, $Ar^3$, and $Ar^4$ are each aromatic selected from the group consisting of a hydrocarbon aromatic radical with from about 6 to about 30 carbon atoms, a pyridyl, an 1,3,5-oxadiazolyl, a quinolyl, and a thienyl, and wherein said aromatic optionally further contains a substituent selected from the group consisting of hydrogen, alkyl with from 1 to about 10 carbon atoms, alkoxy with from about 2 to about 10 carbon atoms, a halogen, and a cyano group.

3. A triazine compound in accordance with claim 1 wherein $Ar^1$, $A^2$, $Ar^3$, and $Ar^4$ are each aryl selected from the group consisting of phenyl, a stilbenyl, a biphenylyl, a naphthyl, and a terphenylyl, and wherein said aryl optionally contains a substituent selected from the group consisting of hydrogen, an alkyl group with from 1 to about 6 carbon atoms, an alkoxy group with from 1 to about 6 carbon atoms, a halogen, and a cyano group.

4. A triazine compound in accordance with claim 1 wherein the triazine compound is represented by formula

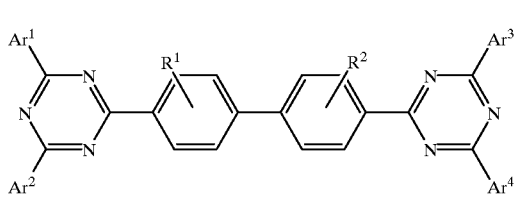

(II)

wherein $Ar^1$, $Ar^2$, $Ar^3$, and $Ar^4$ are each aryl; $R^1$ and $R^2$ are selected from the group consisting of hydrogen, aliphatic, halogen, and a cyano group.

5. A triazine in accordance with claim 4 wherein $Ar^1$, $Ar^2$, $Ar^3$, and $Ar^4$ are selected from the group consisting of a phenyl, a stilbenyl, a biphenylyl, a naphthyl, a pyridyl, a quinolyl, and 1,3,5-oxadiazolyl, and wherein the aryl group optionally contains a substituent selected from the group consisting of hydrogen, an alkyl group with from 1 to about 6 carbon atoms, an alkoxy group with from 1 to about 6 carbon atoms, a dialkylamino group with from about 1 to about 3 carbon atoms, halogen, or a cyano group.

6. A triazine in accordance with claim 4 wherein $Ar^1$, $A^2$, $Ar^3$, and $Ar^4$ are each an aromatic hydrocarbon group containing from about 6 to about 30 carbon atoms.

7. A triazine in accordance with claim 4 wherein $R^1$ and $R^2$ are selected from the group consisting of hydrogen, methyl, and a halogen atom.

8. A triazine in accordance with claim 4 wherein $Ar^1$, $Ar^2$, $Ar^3$, and $Ar^4$ are each an aryl group selected from the group consisting of a phenyl, a stilbenyl, a biphenylyl, a naphthyl, which aryl contains a substituent selected from the group consisting of hydrogen, an alkyl group with from 1 to about 6 carbon atoms, an alkoxy group with from 1 to about 6 carbon atoms, a dialkylamino group with from about 1 to about 3 carbon atoms, a halogen, and a cyano group; and $R^1$ and $R^2$ are selected from the group consisting of hydrogen, methyl, and a halogen atom.

9. A triazine compound in accordance with claim 1 wherein the triazine compound is represented by formula of

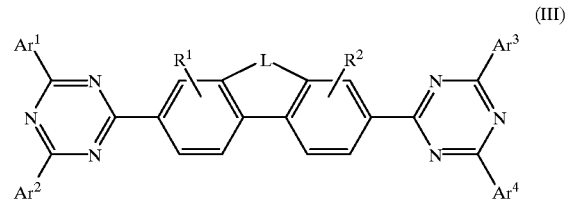

(III)

wherein $Ar^1$, $A^2$, $Ar^3$, and $Ar^4$ are each an aromatic hydrocarbon group or a heteroaromatic group; $R^1$ and $R^2$ are substituents, selected from the group consisting of hydrogen, an alkyl group, an alkoxy group, a halogen, and a cyano group; and L is divalent group selected from the group consisting of an alkylene, a vinylene, an oxygen atom, a sulfur atom, and —Si(R'R'')—, wherein R' and R'' are selected from the group consisting of hydrogen, alkyl, alkoxy, and aryl.

10. A triazine in accordance with claim 9 wherein L is a divalent group of —C(R'R'')—, wherein R' and R'' are selected from the group consisting of hydrogen, alkyl, a phenyl, an alkylphenyl, an alkoxy, an alkoxyphenyl, and a heteroaromatic group.

11. A compound in accordance with claim 9 wherein $Ar^1$, $A^2$, $Ar^3$, and $Ar^4$ are each an aryl group selected from the group consisting of a phenyl, a stilbenyl, a biphenylyl, and a naphthyl.

12. A triazine compound in accordance with claim 9 wherein $Ar^1$, $Ar^2$, $Ar^3$, and $Ar^4$ are each an aryl group selected from the group consisting of a phenyl, a stilbenyl, a biphenylyl, a naphthyl, which aryl further contains a substituent selected from the group consisting of hydrogen, an alkyl group with from 1 to about 6 carbon atoms, an alkoxy group with from 1 to about 6 carbon atoms, and a dialkylamino group with from about 1 to about 3 carbon atoms; and $R^1$ and $R^2$ are selected from the group consisting of hydrogen, alkyl, and halogen; and L is a divalent group of —C(R'R")—, wherein R' and R" are selected from the group consisting of hydrogen, alkyl, a phenyl, an alkylphenyl, an alkoxy, and an alkoxyphenyl.

13. A triazine compound in accordance with claim 1 wherein said triazine compound is selected from the group consisting of 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-methoxyphenyl-1,3,5-triazinyl)]-1,1'-biphenyl, 4,4'-bis-[2-(4,6-di-m-methoxyphenyl-1,3,5-triazinyl)]-1,1'-biphenyl, 4,4'-bis-[2-(4-β-naphthyl-6-phenyl-1,3,5-triazinyl)]-1,1'-biphenyl, 4,4'-bis-[2-(4,6-di-biphenylyl-1,3,5-triazinyl)]-1,1'-biphenyl, 4-[2-(4,6-di-phenyl-1,3,5-triazinyl)]-4'-[2-(4,6-di-m-tolyl-1,3,5-triazinyl)]-1,1'-biphenyl, 2,7-bis-[2-(4,6-di-phenyl-1,3,5-triazinyl)]fluorene, 2,7-bis-[2-(4,6-di-phenyl-1,3,5-triazinyl)]-9,9-dimethylfluorene, 2,7-bis-[2-(4,6-di-phenyl-1,3,5-triazinyl)]-9,9-diethylfluorene, 2,7-bis-[2-(4,6-di-phenyl-1,3,5-triazinyl)]-9,9-diphenylfluorene, 2,7-bis-[2-(4,6-di-phenyl-1,3,5-triazinyl)]-9,10-dihydraphenanthrene, 4,9-bis-[2-(4,6-di-phenyl-1,3,5-triazinyl)]dibenzofuran, 4,9-bis-[2-(4,6-di-phenyl-1,3,5-triazinyl)]dibenzothiophene, and 2,7-bis-[2-(4,6-di-phenyl-1,3,5-triazinyl)]-9,9-dimethyl-9-silafluorene.

14. A triazine compound in accordance with claim 1 wherein said triazine compound is selected from the group consisting of 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-methoxyphenyl-1,3,5-triazinyl)]-1,1'-biphenyl, 4,4'-bis-[2-(4,6-di-m-methoxyphenyl-1,3,5-triazinyl)]-1,1'-biphenyl, 4,4'-bis-[2-(4-β-naphthyl-6-phenyl-1,3,5-triazinyl)]-1,1'-biphenyl, 4,4'-bis-[2-(4,6-di-biphenylyl-1,3,5-triazinyl)]-1,1'-biphenyl, 2,7-bis-[2-(4,6-di-phenyl-1,3,5-triazinyl)]fluorene, and 2,7-bis-[2-(4,6-di-phenyl-1,3,5-triazinyl)]-9,9-dimethylfluorene.

15. A triazine of the formula

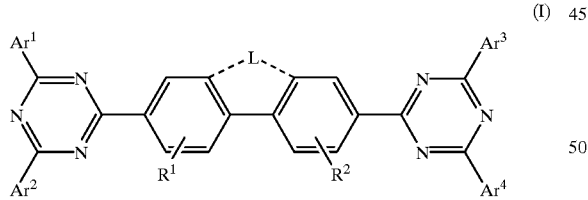

(I)

wherein $Ar^1$, $Ar^2$, $Ar^3$ and $Ar^4$ are each independently aryl; $R^1$ and $R^2$ are each aryl, aliphatic, hydrogen, halogen, or cyano; and L is a divalent moiety.

16. A triazine in accordance with claim 15 wherein aryl is aromatic with from 6 to about 30 carbon atoms.

17. A triazine in accordance with claim 15 wherein aliphatic is alkyl.

18. A triazine in accordance with claim 17 wherein alkyl contains from 1 to about 25 carbon atoms.

19. A triazine in accordance with claim 15 wherein aliphatic is alkoxy.

20. A triazine in accordance with claim 19 wherein alkoxy contains from about 2 to about 25 carbon atoms.

21. A triazine in accordance with claim 15 wherein $R^1$ and $R^2$ are each hydrogen, alkyl, or alkoxy.

22. A triazine of the formula

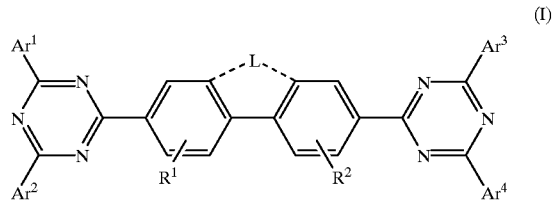

(I)

wherein each $Ar^1$, $A^2$, $Ar^3$ and $Ar^4$ are aliphatic; $R^1$ and $R^2$ are each aryl, aliphatic, hydrogen, halogen, or cyano, and L is a divalent moiety.

23. A triazine in accordance with claim 22 wherein aliphatic is alkyl or alkoxy.

24. A triazine in accordance with claim 15 wherein L is alkylene.

25. A triazine in accordance with claim 15 wherein L is vinylene.

26. A triazine in accordance with claim 15 wherein L is an oxygen atom or a sulfur atom.

27. A triazine of the formulas or as represented by the formulas

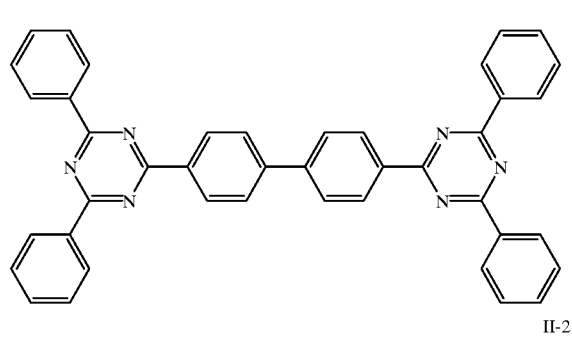

II-1

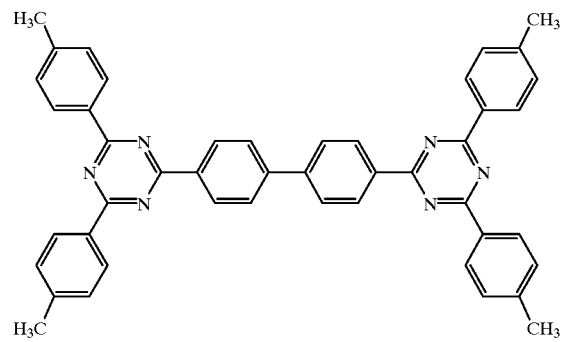

II-2

II-3
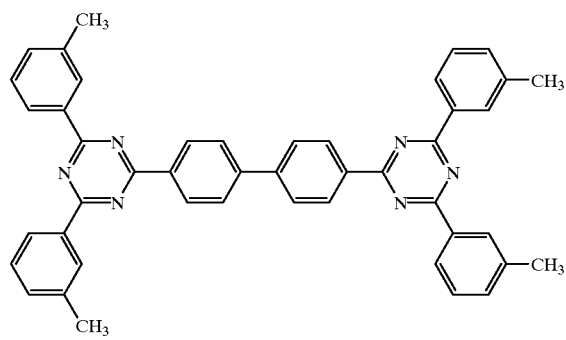
II-4
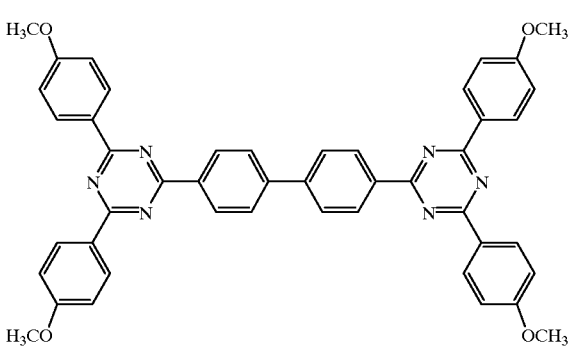
II-5
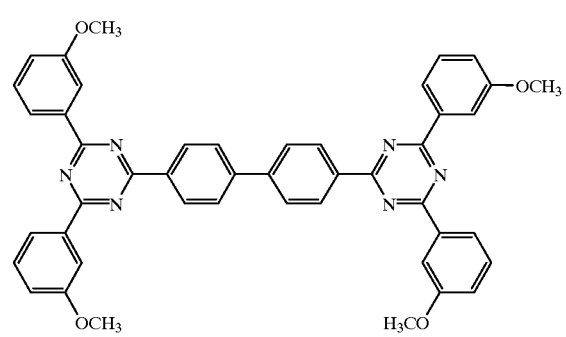
II-6
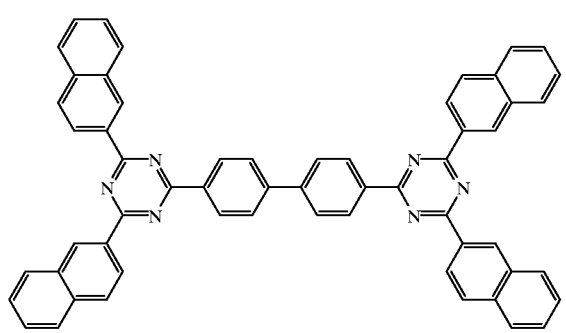
II-7
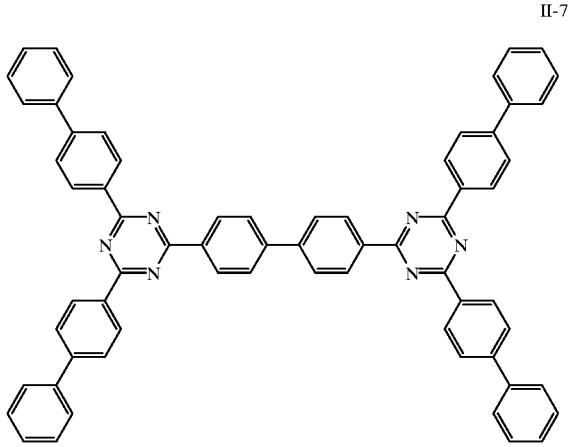
II-8
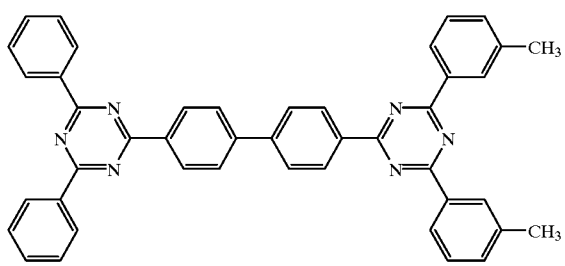
III-1
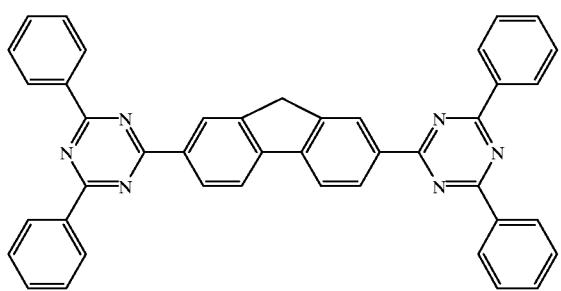
III-2
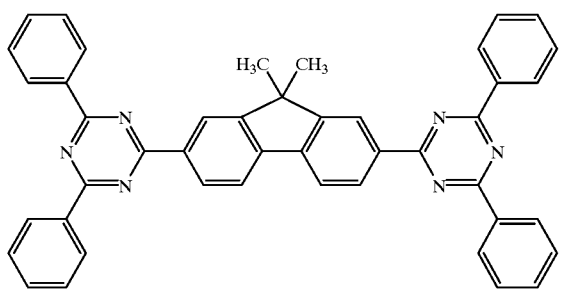

III-3
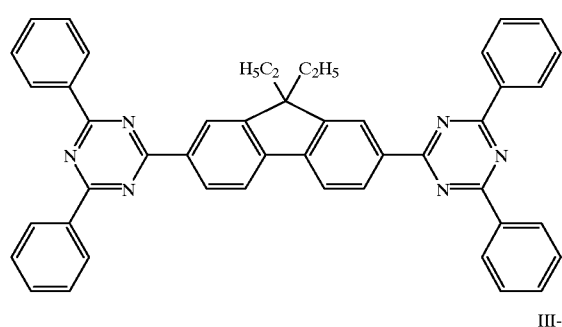
III-4
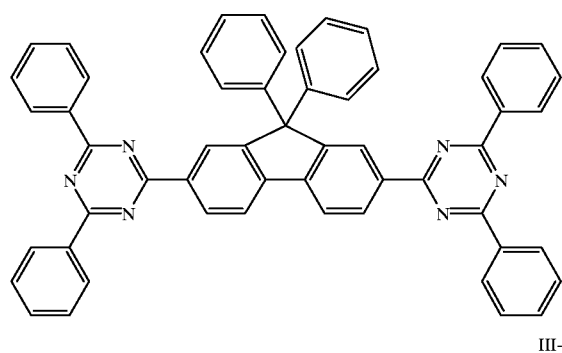
III-5
III-6
III-7
III-8
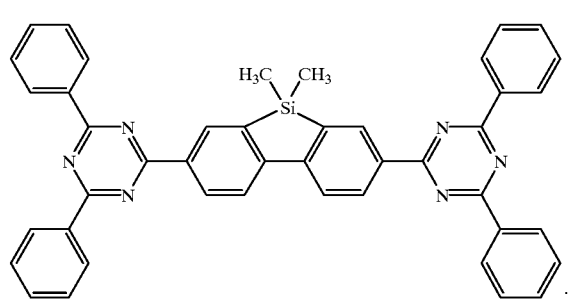
28. A triazine in accordance with claim 34 and as represented by
II-1
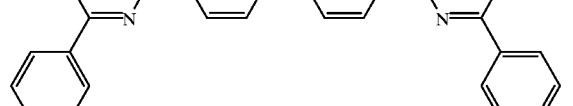
II-2
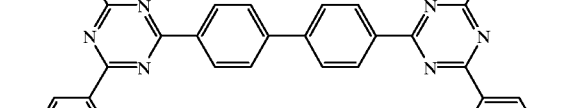
II-3

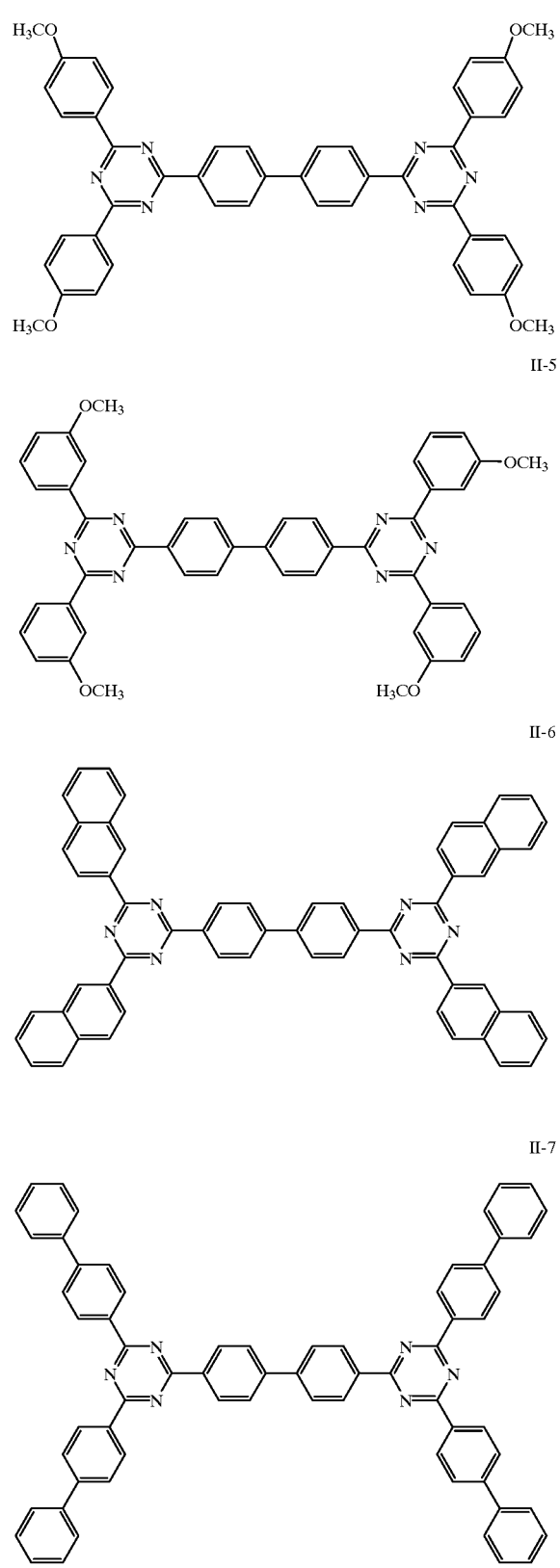
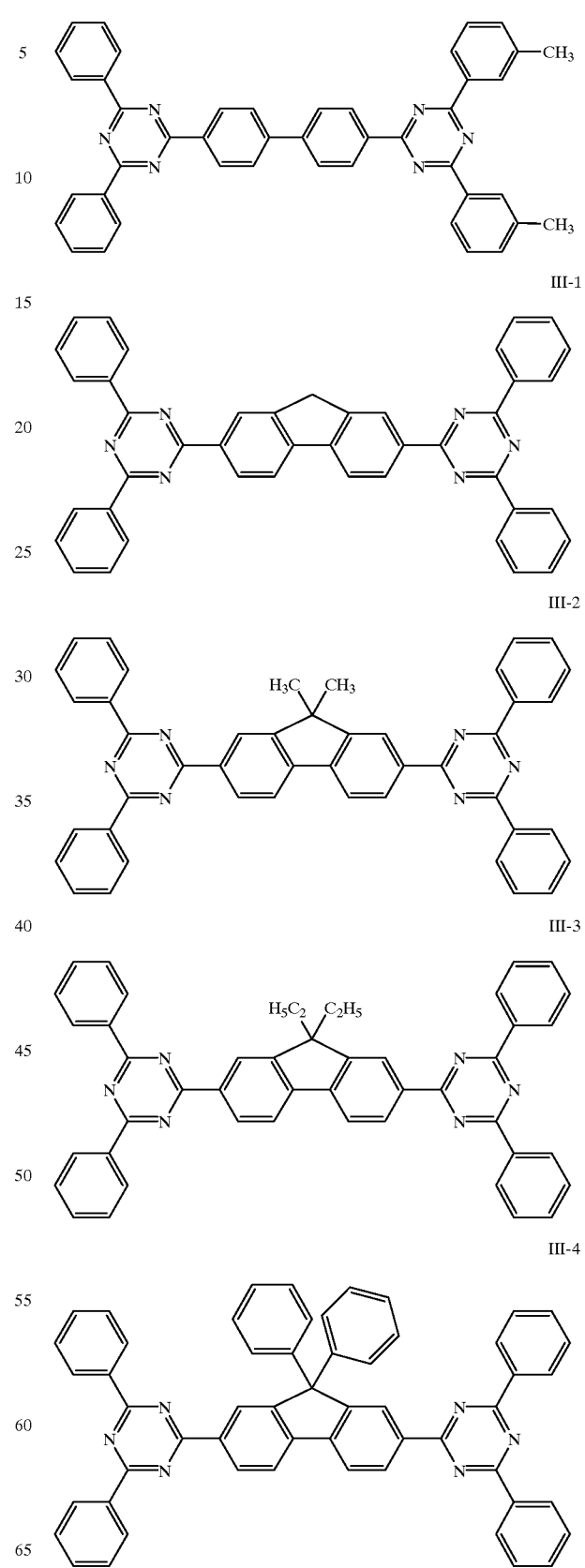

-continued

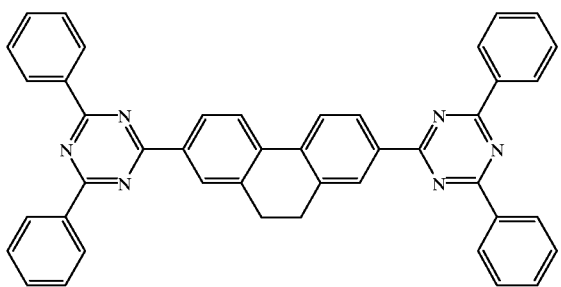

III-5

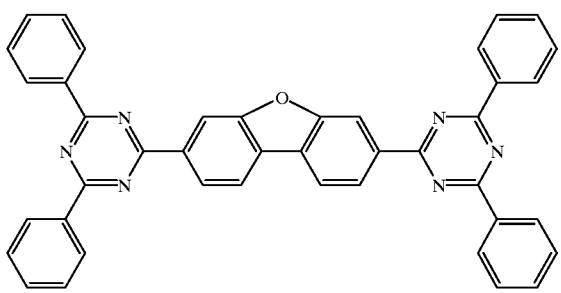

III-6

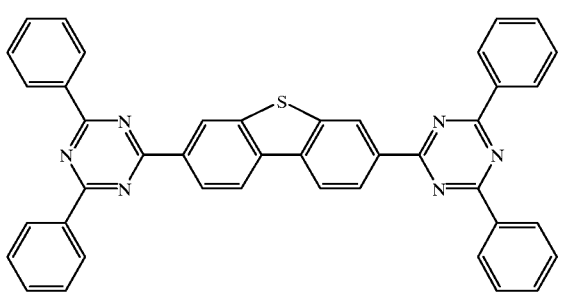

III-7

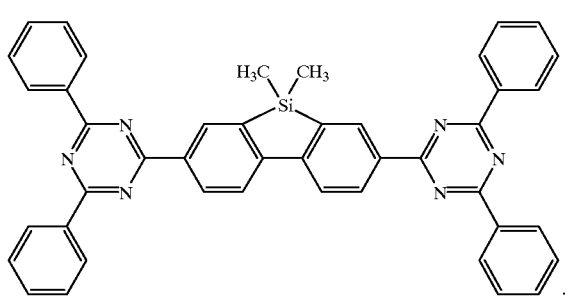

III-8

29. A triazine in accordance with claim 1 wherein L is selected from the group consisting of an alkylene, a vinylene, an oxygen atom, a sulfur atom, and —Si(R'R")—, wherein R' and R" are selected from the group consisting of hydrogen, alkyl, alkoxy, and aryl.

30. A triazine in accordance with claim 15 wherein L is selected from the group consisting of an alkylene, a vinylene, an oxygen atom, a sulfur atom, and —Si(R'R")—, wherein R' and R" are selected from the group consisting of hydrogen, alkyl, alkoxy, and aryl.

31. A triazine in accordance with claim 4 wherein aliphatic is alkyl.

32. A triazine in accordance with claim 4 wherein aliphatic is alkoxy.

33. A triazine in accordance with claim 4 wherein aryl is a heteroaromatic.

34. A triazine compound of the formula

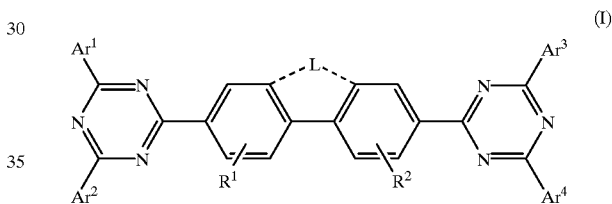

(I)

wherein $Ar^1$, $Ar^2$, $Ar^3$, and $Ar^4$ are each an aryl, aliphatic, or mixtures thereof; $R^1$ and $R^2$ are selected from the group consisting of hydrogen, alkyl, aryl, alkoxy, halogen, and cyano; and wherein L is a divalent group selected from the group consisting of alkylene, an oxygen atom, a sulfur atom, —Si(R'R")—, wherein R' and R" are selected from the group consisting of hydrogen, alkyl, alkoxy, and aryl and the like; and preferably L is —C(R'R")—, wherein R' and R" is a hydrogen atom, an alkyl group containing from 1 to about 10 carbon atoms.

\* \* \* \* \*